United States Patent [19]

Kadin

[11] 4,296,129

[45] Oct. 20, 1981

[54] (CARBOXYACYLAMINO)PHENYLALKENA-MIDES AND ESTERS THEREOF AS SRS-A ANTAGONISTS

[75] Inventor: Saul B. Kadin, New London, Conn.

[73] Assignee: Pfizer, Inc., New York, N.Y.

[21] Appl. No.: 201,894

[22] Filed: Oct. 29, 1980

[51] Int. Cl.$^3$ .................. A61K 31/24; C07C 101/447; C07C 101/453
[52] U.S. Cl. ..................................... 424/309; 424/316; 424/319; 560/37; 562/442; 260/501.11; 260/326.8; 544/107; 546/184
[58] Field of Search ........................ 560/37; 562/442; 424/309, 319

[56] References Cited

U.S. PATENT DOCUMENTS

| | | | |
|---|---|---|---|
| 625,159 | 5/1899 | Einhorn | 560/37 |
| 3,993,679 | 11/1976 | Hall et al. | 560/37 |
| 4,036,837 | 7/1977 | Sellsted et al. | 560/37 |

*Primary Examiner*—G. T. Breitenstein
*Attorney, Agent, or Firm*—Charles J. Knuth; Peter C. Richardson; J. Trevor Lumb

[57] ABSTRACT

Certain new propenamides and 2-butenamides having a (carboxyalkanamido)phenyl or a (carboxyalkenamido)-phenyl group at the 3-position, and certain esters thereof, and their use for antagonizing the spasmogenic activity of slow-reacting substance of anaphylaxis (SRS-A) in a human subject. In particular, the compounds of the invention are useful for preventing and treating certain obstructive airways diseases, notably allergic bronchial asthma, allergic rhinitis and certain skin disorders, in human subjects.

27 Claims, No Drawings

(CARBOXYACYLAMINO)PHENYLALKENAMIDES AND ESTERS THEREOF AS SRS-A ANTAGONISTS

BACKGROUND OF THE INVENTION

This invention relates to new chemical compounds, and more particularly it relates to derivatives of propenamide, 2-methylpropenamide, 2-butenamide and 2-methyl-2-butenamide. Said derivatives are further substituted on the nitrogen atom by an alkyl or cycloalkyl group, and at the 3-position by a (carboxyalkanamido)phenyl or (carboxyalkenamido)phenyl group. These compounds are useful as antagonists of the slow-reacting substance of anaphylaxis (SRS-A).

It is known that certain substances, known as mediators of anaphylaxis, play an important role in inducing an allergic reaction, such as bronchospastic attack or allergic rhinitis, in a human subject. Two examples of such mediators are histamine and the slow-reacting substance of anaphylaxis (SRS-A), the latter substance being a very important mediator in allergic bronchial asthma. SRS-A is a substance which is synthesized and released in or near target tissues, in a sensitive (allergic) human subject, shortly after challenge with the appropriate antigen. The human bronchus is particularly sensitive to SRS-A.

Rational approaches to drug therapy to prevent, remove or ameliorate the symptoms of allergic reactions have focussed on either blocking the release of mediators of anaphylaxis, or, on the other hand, on antagonizing their effects. Disodium cromoglycate (The Merck Index, Merck & Co., Inc., Rahway, New Jersey, 9th Edition, 1976, 2585) is a drug which has recently been introduced and which blocks the release of mediators of anaphylaxis, and commercially available drugs which antagonize histamine (antihistamines) are well-known (e.g. methapyrilene, diphenhydramine, chlorpheniramine). Conversely, there is a paucity of substances known which antagonize SRS-A, and none of them is used in clinical practice today. One agent has been widely studies (FPL 55712-*Agents and Actions*, 9, 133 [1979]).

SUMMARY OF THE INVENTION

This invention provides novel alkenamide compounds of the formula

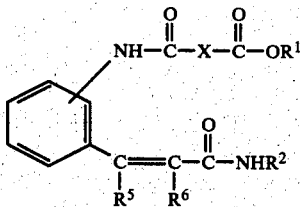

and the pharmaceutically-acceptable salts thereof;
wherein $R^1$ is selected from the group consisting of hydrogen, alkyl having 1 to 4 carbons, and —CH$_2$—CH$_2$—NR$^3$R$^4$, wherein $R^3$ and $R^4$ are each alkyl having 1 to 3 carbons;
$R^2$ is selected from the group consisting of alkyl having 8 to 15 carbons and cycloalkyl having from 6 to 12 carbons;
$R^5$ and $R^6$ are selected from the group consisting of hydrogen and methyl;
and X is selected from the group consisting of cis-vinylene, ethylene and

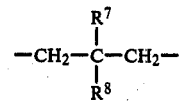

wherein $R^7$ and $R^8$ are each selected from the group consisting of hydrogen and methyl.

When either of $R^1$ and $R^2$ is an alkyl group, it can be straight-chain or branched-chain. $R^3$ and $R^4$ can be straight-chain or branched-chain.

This invention also provides a method of antagonizing the spasmogenic activity of the slow-reacting substance of anaphylaxis (SRS-A) in a human subject, which comprises administering to said subject an effective amount of a compound of the formula I, or a pharmaceutically-acceptable salt thereof. The compounds of formula I are antagonists of the effects of slow-reacting substance of anaphylaxis (SRS-A), and they are useful therefore for preventing and treating certain obstructive airways diseases, notably allergic bronchial asthma, allergic rhinitis and certain skin disorders in human subjects.

Still further, this invention provides pharmaceutical compositions, suitable for administration to a human subject, which comprise a pharmaceutically-acceptable carrier and a compund of the formula I, or a pharmaceutically-acceptable salt thereof.

A preferred group of compounds of this invention is the group of compounds of formula I, wherein $R^1$ is hydrogen, $R^2$ is said alkyl and X is cis-vinylene. Within this group, the compounds wherein $R^5$ and $R^6$ are both hydrogen are particularly preferred. An especially preferred individual compound is N-decyl-3-(3-[cis-3-carboxypropenamido]phenyl)propenamide, the compound of formula I, wherein $R^1$, $R^5$ and $R^6$ are each hydrogen, $R^2$ is decyl, X is cis-vinylene and the two groups on the phenyl ring are in a meta relationship to each other.

DETAILED DESCRIPTION OF THE INVENTION

In this specification, the compounds of formula I, and several of the intermediates leading thereto, are named as derivatives of propenamide, 2-methyl-propenamide, 2-butenamide and 2-methyl-2-butenamide, which have structures II, III, IV and V, respectively, viz:

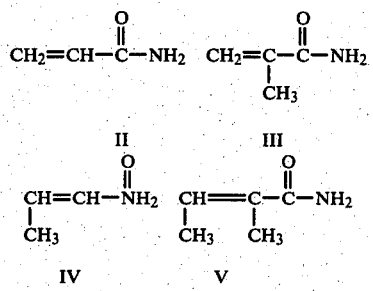

The derived term "propenamido" refers to the radical —NH—CO—CH=CH$_2$, and the terms "propanamido" and "butanamido" refer to the radicals —NH—CO—CH$_2$—CH$_3$ and —NH—CO—CH$_2$—CH$_2$—CH$_3$, respectively.

When $R^2$ is an alkyl group, it can be straight-chain or branched-chain. However, in this specification, when the $R^2$ group is an alkyl group it is named according to the system of the Chemical Abstracts Service of the Americal Chemical Society. This means that within a given name each individual term denotes a straight-chain radical, having the free valency at the 1-position. For example decyl denotes the group $CH_3(CH_2)_8CH_2$—, the group $(CH_3CH_2CH_2CH_2CH_2)_2CH$— is named 1-pentylhexyl and the group $(CH_3)_2CHCH_2CH_2CH_2CH_2CH_2$— is named 6-methylheptyl.

The alkenamide compounds of formula I, wherein $R^1$ is hydrogen, can be prepared by reaction of the appropriate amine of the formula

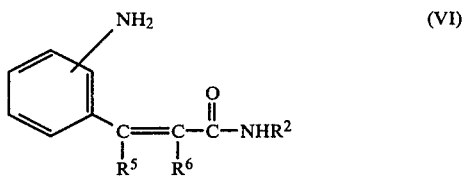

with a cyclic anhydride selected from the group consisting of maleic anhydride, succinic anhydride, glutaric anhydride, 3-methylglutaric anhydride and 3,3-dimethylglutaric anhydride. The reaction is conveniently carried out by heating substantially equimolar quantities of the reagents in a reaction-inert solvent. A wide variety of solvents can be used for this purpose. The major requirements for such a solvent are that it substantially dissolves at least one of the reactants, it does not adversely interact with either of the reactants or the product, and the product can be recovered from it at the end of the reaction. Typical solvents which can be used are hydrocarbons, such as cyclohexane, decalin, tetralin, benzene, toluene and xylene; ethers such as 1,2-dimethoxyethane and dioxane; ketones, such as methyl isobutyl ketone and cyclohexanone; low molecular weight esters, such as ethyl acetate and butyl acetate; alkanols, such as methanol, ethanol and isopropanol; and mixtures of these solvents. The reaction is usually conducted at a temperature in the range from about 60° to about 150° C., and preferably from about 80° to 120° C. At about 90° C. the reaction is often complete within a few minutes, although in some instances it is necessary to continue the reaction for up to two hours. After the reaction is substantially complete, the compound of formula I is recovered by conventional techniques. For example, if the compound of formula I is out of solution it can be recovered by filtration; otherwise the solvent can be removed by evaporation.

Alternatively, the compound of formula I can be obtained by contacting substantially equimolar quantities of a compound of formula VI and one of the aforesaid cyclic anhydrides, at elevated temperature, in the molten state. Temperatures in the range from about 60° to about 150° C. are commonly used, with temperatures from about 80° to 120° C. being preferred. At about 90° C., the reaction is often complete within a few minutes although in some instances it is necessary to continue the reaction for up to two hours. At the end of the reaction, the product can be recovered by conventional methods. One convenient method involves cooling the reaction medium and then adding about a 10-fold excess of a solvent in which the product is only slightly soluble but in which the starting materials are readily soluble. The product is recovered by filtration. The particular solvent which is used for this purpose will vary according to the precise structure of the product, but an appropriate solvent will be chosen readily by one skilled in the art. Lower alkanols, such as methanol, ethanol and isopropanol, and low molecular weight esters, such as ethyl acetate, are commonly used.

A compound of formula I can be purified by conventional means, e.g. chromatography and/or recrystallization from an appropriate solvent.

The compounds of formula VI are obtained by reduction of the corresponding nitro compound of the formula

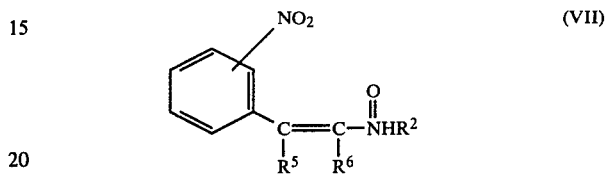

A convenient way of carrying out this reduction is to use iron in glacial acetic acid. Thus, in one method, the compound of formula VII is dissolved in glacial acetic acid, the solution is heated to 85°–90° C., and then an approximately equal weight of iron powder is added portionwise with stirring, during about 10 to 15 minutes. The reaction mixture is stirred an additional 15 minutes and then the solids are removed by filtration. The solids are washed with acetic acid, and then the combined acetic acid solutions are evaporated to give the compound of formula VI. In many instances, the compound of formula VI is sufficiently pure in its crude state for reaction with the appropriate cyclic anhydride. However, it can be purified by conventional techniques such as chromatography and/or recrystallization, if desired.

The compounds of formula VII can be obtained from the corresponding compound of the formula

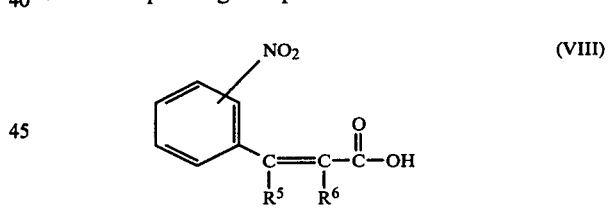

Conversion of a compound of the formula VIII into a compound of the formula VII involves activation of the carboxy group followed by reaction with the appropriate amine of formula $R^2$-$NH_2$.

One convenient way of activating the carboxy group in a compound of formula VIII involves conversion into the corresponding acid chloride. This is normally carried out by heating the acid with about 1.5 molar equivalents of thionyl chloride, in benzene, at reflux temperature, for about two hours. Removal of all volatile materials by evaporation in vacuo then affords the acid chloride in essentially quantitative yield. In most instances the acid chloride is sufficiently pure for direct reaction with the amine of formula $R^2$-$NH_2$; however, it can be purified further by recrystallization from a solvent such as carbon tetrachloride, if desired.

Reaction of the acid chloride of a compound of formula VIII with an amine of formula $R^2$-$NH_2$ is normally accomplished by dissolving the amine in a reaction-inert organic solvent such as tetrahydrofuran, cooling the solution to about 0° C., and then adding a solution of about 0.5 equivalents of the acid chloride, in a small volume of the reaction-inert solvent, dropwise, with stirring, during about 10 to 20 minutes. At a temperature of about 0° to 25° C., the reaction takes about one to about four hours substantially to reach completion. At the end of the reaction, the reaction medium is partitioned between water and a volatile, water-immiscible, organic solvent. The organic solvent is removed, washed with water at pH 7.0 and with water at pH 3.5, and then dried. Removal of the solvent by evaporation in vacuo affords the compound of formula VII.

A second convenient way of activating the carboxy group in a compound of the formula VIII involves formation of a mixed anhydride. Mixed anhydride formation entails suspending or dissolving a carboxylate salt (e.g. the triethylamine salt) in a reaction-inert organic solvent (e.g. dichloromethane) and then adding about one molar equivalent of a hindered alkanoyl chloride (e.g. pivaloyl chloride) or a lower-alkyl chloroformate (e.g. ethyl chloroformate). The reaction is usually carried out at about 0° C., and it normally takes about 30 minutes to one hour to reach completion. Although the mixed anhydride can be isolated by solvent evaporation, it is usual simply to use it in situ for reaction with the amine of formula $R^2$-$NH_2$. In this case a solution of about one molar equivalent of the amine is added to the mixed anhydride solution, dropwise, at about 0° C. The reaction is allowed to proceed for about 30 minutes to one hour at about 0° to 25° C. If a water-immiscible solvent has been used, the product is isolated by washing the solvent with 1 N potassium hydroxide and with water. The solution is then dried and evaporated in vacuo to give the compound of formula VII. If a water-miscible solvent has been used, the product can be isolated by removing the solvent by evaporation in vacuo, replacing it with a water-immiscible sovlent, and then proceding as described above.

The compounds of formula VIII, wherein $R^5$ is hydrogen and $R^6$ is selected from the group consisting of hydrogen and methyl, can be prepared by condensation of the appropriate nitrobenzaldehyde with a phosphorane of the formula

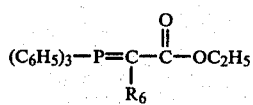
(IX)

followed by basic hydrolysis of the ethyl ester grouping.

The compounds of formula VIII, wherein $R^5$ is methyl and $R^6$ is selected from the group consisting of hydrogen and methyl, can be prepared by reaction of the appropriate nitroacetophenone and a phosphonate compound of the formula

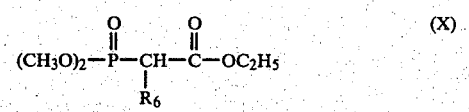
(X)

in the presence of one equivalent of sodium hydride, followed by basic hydrolysis of the ethyl ester grouping.

Some of the compounds of formula VIII are known (see further Baker et al., *Journal of Medicinal Chemistry*, 11, 672 [1968]), and some are commercially available.

The compounds of formula IX are either commercially available or known (see further Isler et al., *Helvetica Chimica Acta*, 40, 1242 [1957]). The compounds of formula X are either commercially available or known (see further Arbusor et al., *Chemische Berichte*, 60, 291 [1927] and *Chemical Abstracts*, 23, 4444 [1929]).

The compounds of formula I, wherein $R^1$ is alkyl, can be prepared by reaction of the corresponding compound of formula I, wherein $R^1$ is hydrogen, with the appropriate diazoalkane. In this case, the free acid is dissolved or suspended in a reaction-inert solvent, and then a slight excess of an ethereal solution of the diazoalkane is added. The reaction mixture is stirred at ambient temperature for about two to 24 hours, and then any excess diazoalkane is decomposed by the addition of a small amount of acetic acid. Removal of the solvent in vacuo affords the required compound of formula I, wherein $R^1$ is alkyl. Suitable solvents for this esterification procedure are those which do not adversely interact with either the starting material or the product, and from which the product can be recovered readily. Typical examples are chlorinated hydrocarbons, such as chloroform and dichloromethane; ethers, such as tetrahydrofuran, dioxane and 1,2-dimethoxyethane; and acetonitrile.

The compounds of formula I, wherein $R^1$ is —$CH_2CH_2$—$NR^3R^4$ can be prepared from the corresponding compound of formula I, wherein $R^1$ is hydrogen, by esterification with a compound of the formula HO—$CH_2CH_2$—$NR^3R^4$. This reaction can be carried out conveniently by first activating the compound of formula I, wherein $R^1$ is hydrogen, by reaction with carbonyldiimidazole. The activated derivative is then reacted with the appropriate 2-(N,N-dialkylamino)ethanol. In a typical procedure, substantially equimolar quantities of a compound of formula I, wherein $R^1$ is hydrogen, and carbonyldiimidazole are reacted for a few minutes at about 60° to 70° C., in a reaction inert solvent such as tetrahydrofuran, and then one to two equivalents of the 2-(N,N-dialkylamino)ethanol are added. After a reaction time of about 15 to 30 minutes at about 60° to 70° C., the solvent is removed. The residue is dissolved in a water-immiscible, volatile solvent and the solution is washed with water and dilute sodium hydroxide, and then it is dried. Evaporation affords the compound of formula I, wherein $R^1$ is —$CH_2$—$CH_2$—$NR^3R^4$.

As will be appreciated by one skilled in the art, a compound of the formula I can exist in one of two geometrical isomers, by virtue of the presence of the double bond to which the substituted phenyl and the CO-$NHR^2$ groups are attached. In one isomer the substituted phenyl group is on the opposite side of the double bond from the —CO-$NHR^2$ group (the trans-isomer); in the other isomer, the substituted phenyl group is on the same side of the double bond as the —CO-$NHR^2$ group (the cis-isomer). Both isomers, and mixtures thereof, are within the scope of this invention. However, the trans-isomers are preferred. Additionally, as will be appreciated by one skilled in the art, if it is desired to prepare a trans-isomer of the formula I, the synthetic sequence VIII to VII to VI to I is carried out starting with a compound of formula VIII, in which the nitrophenyl and the carboxy groups are on opposite sides of the double bond from each other. Conversely, operation of the synthetic scheme VIII to VII to VI to I, starting with a compound of formula VIII in which the nitrophenyl group and the carboxy group are on the same side of the double bond as each other, leads to the cis-isomer.

The compounds of the formula I, wherein $R^1$ is hydrogen, are acidic and they form base salts. All such base salts are within the scope of this invention. They can be prepared by conventional methods for carboxylic acid compounds. For example, they can be prepared readily and conveniently simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, as appropriate, or, in the case of aqueous solutions, by lyophilization. Basic agents suitably employed in salt formation belong to both the organic and inorganic types, and they include ammonia, organic amines, alkali metal hydroxides, alkali metal carbonates, alkali metal bicarbonates, alkali metal hydrides, alkali metal alkoxides, alkaline earth metal hydroxides, alkaline earth metal carbonates, alkaline earth metal hydrides and alkaline earth metal alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazobicyclo[4.3.0]non-5-ene; hydroxides, such as sodium hydroxide; alkoxides, such as sodium methoxide and potassium methoxide; hydrides, such as calcium hydride and sodium hydride; and carbonates, such as potassium carbonate and sodium carbonate.

Additionally, the compounds of formula I, wherein $R^1$ is $-CH_2CH_2-NR^3R^4$, are basic and they will form acid-addition salts. All such acid-addition salts are within the scope of this invention. They can be prepared by conventional methods for tertiary amine compounds. For example, they can be prepared by contacting said compound of formula I, wherein $R^1$ is $-CH_2CH_2-NR^3R^4$, with a stoichiometric amount of the appropriate acid in an appropriate solvent. The salt can then be recovered by filtration, by precipitation with a non-solvent followed by filtration, by evaporation of the solvent, as appropriate. Acid-addition salts of compounds of formula I, wherein $R^1$ is $-CH_2-CH_2-NR^3R^4$, can be prepared from both inorganic and organic acids, and typical salts are the hydrochloride, hydrobromide, hydroiodide, sulfate, bisulfate, phosphate, acetate, maleate, fumarate, oxalate, lactate, tartrate, citrate, gluconate and 4-toluenesulfonate.

As indicated hereinbefore, the compounds of formula I are of value as antagonists of the slow-reacting substance of anaphylaxis (SRS-A). This activity can be detected and evaluated by methods known in the art. In one method, the ability of a compound of formula I to antagonize SRS-A induced contractions in isolated guinea pig ileal muscle is measured. Terminal ileum segments, 2.5 cm. long are removed from Reed-Willet guinea pigs, 350–450 g., and suspended in 10 ml. muscle baths containing Tyrode's solution (NaCl-136.9 mM, KCl-2.68 mM, $CaCl_2$-1.8 mM, $NaH_2PO_4$-0.42 mM, $MgCl_2$-2.0 mM, $NaHCO_3$-11.9 mM, glucose-5.5 mM) saturated with 95% $O_2$-5% $CO_2$ and maintained at 38° C. The tissue is attached by silk thread to a Statham force displacement transducer (FT 0.03) under 2 g. tension and muscle activity is recorded via a Grass Model 5 polygraph. For initial testing submaximal contractions to SRS-A ($\sim 1$ unit/ml.) are obtained in a total of six preparations (three from each of two animals). Each antagonist is added to all baths one minute prior to the addition of SRS-A at a concentration of $10^{-4}$ M, and the percentage inhibition of contraction is measured.

The ability of the compounds of formula I to antagonize the effects of SRS-A makes them useful for inhibiting the symptoms induced by SRS-A in a human subject. The compounds are valuable therefore in the prevention and treatment of such disease states in which SRS-A is the causative factor, e.g. skin disorders, allergic rhinitis, and obstructive airways diseases. The compounds are particularly valuable in the prevention and treatment of allergic bronchial asthma.

A compound of formula I, or a pharmaceutically-acceptable salt thereof, can be administered to a human subject either alone, or, preferably, in combination with pharmaceutically-acceptable carriers or diluents, in a pharmaceutical composition, according to standard pharmaceutical practice. A compound can be administered orally or parenterally. Parenteral administration includes intravenous, intramuscular, intraperitoneal, subcutaneous and topical administration, and also administration by inhalation and insufflation.

In a pharmaceutical composition comprising a compound of formula I, or a pharmaceutically-acceptable salt thereof, the weight ratio of carrier to active ingredient will normally be in the range from 1:6 to 6:1, and preferably 1:2 to 4:1. However, in any given case, the ratio chosen will depend on such factors as the solubility of the active component, the dosage contemplated and the precise route of administration.

For oral use of an SRS-A antagonist of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic. For administration by inhalation or insufflation, it is convenient to prepare an aqueous or partially aqueous solution of a compound of formula I or salt thereof, and then this solution is administered in the form of an aerosol.

When a compound of formula I or salt thereof is used as an SRS-A antagonist in a human subject, the daily dosage will normally be determined by the prescribing physician. Moreover, the dosage will vary according to the age, weight and response of the individual patient, as well as the severity of the patient's symptoms. However, in most instances, an effective daily dosage will be in the range from about 0.02 g. to about 1.0 g., and preferably 0.05 g. to 0.5 g., in single or divided doses. On the other hand, it may be necessary to use dosages outside these limits in some cases.

The following examples are provided solely for the purpose of further illustration. Infrared (IR) spectra were measured as potassium bromide discs (KBr discs), and diagnostic absorption bands are reported in reciprocal centimeters (cm$^{-1}$). Nuclear magnetic resonance spectra (NMR) were measured in deuterochloroform (CDCl$_3$), perdeutero dimethyl sulfoxide (DMSO-d$_6$), deuterated trifluoroacetic acid (CF$_3$COOD) or perdeutero pyridine (C$_5$D$_5$N), and peak positions are expressed in parts per million (ppm) downfield from internal tetramethylsilane. The following abbreviations for peak shaps are used: s, singlet; d, doublet; t, triplet; q, quartet; and m, multiplet.

EXAMPLE 1

N-Decyl-3-(3-[cis-3-carboxypropenamido]phenyl)-propenamide

A stirred mixture of 0.907 g. of N-decyl-3-(3-aminophenyl)propenamide and 25 ml. of benzene was heated on a steam bath until a solution was obtained. To this solution was then added 0.358 g. of maleic anhydride in one portion. In about 30 seconds a solid precipitated. The mixture was allowed to cool and then the solid was recovered by filtration. The solid was recrystallized from acetic acid, to give 1.1 g. (92% yeild) of the title compound, melting point 187°–188° C. The IR spectrum (KBr disc) showed absorptions at 3279, 2899, 1724, 1653, 1626, 1587 and 1563 cm$^{-1}$. The NMR spectrum (in DMSO-d$_6$) showed absorptions at 0.91 (m, 3H), 1.24 (s, 16H), 3.18 (m, 2H), 6.50 (m, 4H), 7.42 (m, 4H), 8.11 (m, 2H) and 10.50 (s, 1H) ppm.

Analysis: Calcd. for C$_{23}$H$_{32}$N$_2$O$_4$: C, 68.97; H, 8.05; N, 6.99%. Found: C, 68.58; H, 7.90; N, 6.94%.

EXAMPLE 2

Reaction of the appropriate N-alkyl-3-(aminophenyl) or N-cycloalkyl-3-(aminophenyl) derivative of propenamide, 2-methylpropenamide or 2-butenamide from Preparation 25 with maleic anhydride, succinic anhydride, glutaric anhydride or 3,3-dimethylglutaric anhydride, substantially according to the procedure of Example 1, afforded the compounds in the following Table I. In some instances, toluene was used as the solvent rather than benzene. In those cases in which the product was out of solution at the end of the reaction, it was recovered either by filtration or decantation. In those cases in which the product was not out of solution at the end of the reaction, it was recovered by removing the solvent by evaporation in vacuo.

TABLE I

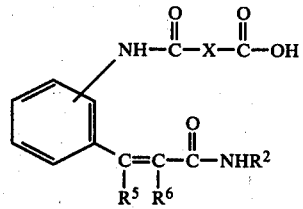

| R$^2$ | R$^5$ | R$^6$ | X | Position of NHCOXCOOH group* | Recrystallization solvent** | Yield (%) | Melting Point (°C.) | Calculated C | Calculated H | Calculated N | Found C | Found H | Found N |
|---|---|---|---|---|---|---|---|---|---|---|---|---|---|
| octyl | H | H | —CH=CH— | 2 | A | 48 | 107–109 | 67.72 | 7.58 | 7.52 | 67.59 | 7.48 | 7.99 |
| octyl | H | H | —CH$_2$CH$_2$— | 2 | A | 57 | 117–118 | 67.34 | 8.09 | 7.48 | 67.61 | 8.03 | 7.49 |
| octyl | H | H | —CH$_2$CH$_2$CH$_2$— | 2 | A | 58 | 113–114 | 68.01 | 8.30 | 7.21 | 67.79 | 8.08 | 7.14 |
| octyl | H | H | —CH$_2$C(CH$_3$)$_2$CH$_2$— | 2 | A | 73 | 165–166 | 69.20 | 8.71 | 6.72 | 68.41 | 8.23 | 6.65 |
| decyl | H | H | —CH=CH— | 4 | B | 33 | 182–184 | 68.97 | 8.06 | 6.99 | 69.24 | 7.92 | 7.00 |
| decyl | H | H | —CH$_2$CH$_2$— | 4 | B | 77 | 220–222 | 68.63 | 8.51 | 6.96 | 68.74 | 8.42 | 6.95 |
| decyl | H | H | —CH$_2$C(CH$_3$)$_2$CH$_2$— | 4 | B | 24 | 173–174 | 70.25 | 9.07 | 6.32 | 70.07 | 8.93 | 6.28 |
| decyl | H | H | —CH$_2$CH$_2$— | 3 | B | 75 | 185–187 | 68.63 | 8.51 | 6.96 | 68.40 | 8.36 | 7.04 |
| decyl | H | H | —CH$_2$CH$_2$CH$_2$— | 3 | B | 73 | 169–171 | 69.21 | 8.71 | 6.72 | 69.02 | 8.58 | 6.57 |
| decyl | H | H | —CH=CH— | 2 | A | 52 | 117–119.5 | 68.97 | 8.05 | 6.99 | 69.23 | 7.99 | 7.06 |
| decyl | H | H | —CH$_2$CH$_2$— | 2 | A | 54 | 117–118 | 68.63 | 8.51 | 6.96 | 68.91 | 8.47 | 6.95 |
| decyl | H | H | —CH$_2$CH$_2$CH$_2$— | 2 | A | 73 | 145–146.5 | 69.20 | 8.71 | 6.72 | 69.00 | 8.38 | 6.60 |
| decyl | H | H | —CH$_2$C(CH$_3$)$_2$CH$_2$— | 2 | A | 60 | 157–158 | 70.24 | 9.07 | 6.30 | 70.07 | 9.05 | 6.29 |
| 1-methyl-decyl | H | H | —CH=CH— | 4 | B | 64 | 195–196 | 69.54 | 8.27 | 6.76 | 69.37 | 8.28 | 6.68 |
| 1-methyl-decyl | H | H | —CH$_2$CH$_2$— | 4 | B | 72 | 217–218 | 69.20 | 8.71 | 6.72 | 69.21 | 8.68 | 6.88 |
| 1-methyl-decyl | H | H | —CH$_2$CH$_2$CH$_2$— | 4 | B | 85 | 211–213 | 69.74 | 8.90 | 6.51 | 69.64 | 8.88 | 6.58 |
| 1-methyl-decyl | H | H | —CH$_2$C(CH$_3$)$_2$CH$_2$— | 4 | C | 58 | 138–140 | 70.71 | 9.23 | 6.11 | 70.57 | 8.95 | 5.87 |
| 1-methyl-decyl | H | H | —CH=CH— | 3 | B | 61 | 182–183 | 69.54 | 8.27 | 6.76 | 69.69 | 8.32 | 6.88 |
| 1-methyl-decyl | H | H | —CH$_2$CH$_2$— | 3 | A | 84 | 145–148 | 69.20 | 8.71 | 6.72 | 68.92 | 8.48 | 6.57 |
| 1-methyl-decyl | H | H | —CH$_2$CH$_2$CH$_2$— | 3 | A | 73 | 150–153 | 69.74 | 8.90 | 6.51 | 69.45 | 8.80 | 6.57 |
| 1-methyl-decyl | H | H | —CH=CH— | 2 | A | 25 | 78–80 | 69.54 | 8.27 | 6.76 | 69.63 | 8.06 | 6.70 |
| 1-methyl-decyl | H | H | —CH$_2$CH$_2$— | 2 | A | 58 | 136–138 | 69.20 | 8.71 | 6.72 | 68.96 | 8.53 | 6.67 |
| 1-methyl-decyl | H | H | —CH$_2$CH$_2$CH$_2$— | 2 | A | 39 | 131–134 | 69.74 | 8.90 | 6.51 | 69.68 | 8.77 | 6.54 |
| 1-methyl-decyl | H | H | —CH$_2$C(CH$_3$)$_2$CH$_2$— | 2 | A | 60 | 177 | 70.71 | 9.23 | 6.11 | 70.43 | 9.13 | 5.91 |
| cyclo- | | | | | | | | | | | | | |

TABLE I-continued $$\underset{\underset{R^5}{|}\phantom{=}\underset{R^6}{|}}{\overset{\displaystyle NH-\overset{O}{\overset{\|}{C}}-X-\overset{O}{\overset{\|}{C}}-OH}{\underset{\displaystyle C=C-\overset{O}{\overset{\|}{C}}-NHR^2}{\text{[phenyl ring]}}}}$$

| R² | R⁵ | R⁶ | X | Position of NHCOXCOOH group* | Recrystallization solvent** | Yield (%) | Melting Point (°C.) | Calculated C | Calculated H | Calculated N | Found C | Found H | Found N |
|---|---|---|---|---|---|---|---|---|---|---|---|---|---|
| cyclo-heptyl | H | H | —CH=CH— | 4 | D | 12 | 182–183 | 67.40 | 6.79 | 7.86 | 67.47 | 6.88 | 7.89 |
| cyclo-heptyl | H | H | —CH=CH— | 3 | B | 55 | 213 | 67.40 | 6.79 | 7.86 | 67.39 | 6.34 | 7.88 |
| cyclo-heptyl | H | H | —CH₂CH₂— | 3 | A | 79 | 180–180.5 | 67.02 | 7.31 | 7.82 | 66.94 | 7.34 | 8.03 |
| cyclo-heptyl | H | H | —CH₂CH₂CH₂— | 3 | A | 47 | 179–181 | 67.72 | 7.58 | 7.52 | 67.88 | 7.55 | 7.64 |
| cyclo-heptyl | H | H | —CH₂C(CH₃)₂CH₂— | 3 | C | 59 | 160–162 | 68.97 | 8.05 | 6.99 | 69.01 | 8.04 | 6.97 |
| cyclodo-decyl | H | H | —CH=CH— | 4 | B | 50 | 191–193 | 70.39 | 8.03 | 6.57 | 70.80 | 7.95 | 6.75 |
| cyclodo-decyl | H | H | —CH₂CH₂— | 4 | B | 66 | 235 | 70.06 | 8.47 | 6.54 | 69.92 | 8.17 | 6.51 |
| cyclodo-decyl | H | H | —CH₂C(CH₃)₂CH₂— | 4 | A | 60 | 186–188 | 71.46 | 8.99 | 5.95 | 71.12 | 9.01 | 6.27 |
| cyclodo-decyl | H | H | —CH=CH— | 3 | A | 19 | 172–174 | 70.39 | 8.03 | 6.57 | 70.31 | 7.85 | 6.54 |
| cyclodo-decyl | H | H | —CH₂CH₂CH₂— | 3 | A | 60 | 161–163 | 70.56 | 8.56 | 6.33 | 70.41 | 8.27 | 6.26 |
| octyl | H | CH₃ | —CH=CH— | 4 | E | 66 | 182.5–183.5 | 68.36 | 7.82 | 7.25 | 68.30 | 7.77 | 7.25 |
| octyl | H | CH₃ | —CH=CH— | 3 | A | 65 | 158–159 | 68.36 | 7.82 | 7.25 | 68.35 | 7.61 | 7.46 |
| octyl | H | CH₃ | —CH₂CH₂CH₂— | 3 | C | 27 | 90.5–91.5 | 68.62 | 8.51 | 6.96 | 68.92 | 8.44 | 7.09 |
| decyl | H | CH₃ | —CH=CH— | 4 | E | 76 | 184.5–185.5 | 69.53 | 8.27 | 6.76 | 69.23 | 8.15 | 6.64 |
| decyl | H | CH₃ | —CH₂CH₂— | 4 | E | 71 | 186.5–187.5 | 69.20 | 8.71 | 6.73 | 69.53 | 8.64 | 6.67 |
| decyl | H | CH₃ | —CH=CH— | 3 | C | 70 | 125–126 | 69.52 | 8.27 | 6.76 | 69.60 | 8.38 | 6.67 |
| decyl | H | CH₃ | —CH₂CH₂— | 3 | C | 47 | 113–114 | 69.20 | 8.71 | 6.73 | 69.20 | 8.88 | 6.75 |
| decyl | H | CH₃ | —CH₂CH₂CH₂— | 3 | C | 78 | 98–99.5 | 69.73 | 8.90 | 6.51 | 69.31 | 8.73 | 6.49 |
| 1-methyl-decyl | H | CH₃ | —CH=CH— | 4 | E |  | 163–164 | 70.06 | 8.47 | 6.54 | 69.78 | 8.40 | 6.51 |
| 1-methyl-decyl | H | CH₃ | —CH=CH— | 3 | A |  | 116.5–117.5 | 70.06 | 8.47 | 6.54 | 70.11 | 8.49 | 6.52 |
| cyclo-heptyl | H | CH₃ | —CH=CH— | 4 | E | 48 | 117.5 | 68.08 | 7.08 | 7.56 | 68.06 | 6.91 | 7.62 |
| cyclo-heptyl | H | CH₃ | —CH₂CH₂— | 4 | E | 58 | 196 | 67.72 | 7.58 | 7.52 | 67.72 | 7.54 | 7.46 |
| decyl | CH₃ | H | —CH=CH— | 4 | A | 64 | 161–163 | 69.54 | 8.27 | 6.76 | 69.97 | 8.26 | 6.82 |
| decyl | CH₃ | H | —CH₂CH₂CH₂— | 4 | A | 53 | 156–157 | 69.74 | 8.90 | 6.51 | 69.80 | 8.81 | 6.48 |
| 1-methyl-decyl | CH₃ | H | —CH=CH | 4 | F | 53 | 185–186 | 70.06 | 8.47 | 6.54 | 69.90 | 8.32 | 6.52 |
| 1-methyl-decyl | CH₃ | H | —CH₂CH₂CH₂— | 4 | A | 55 | 149.5–151.5 | 70.24 | 9.07 | 6.30 | 69.83 | 9.15 | 6.31 |

*The numeral in this column indicates the position of the NHCOXCOOH group on the phenyl ring; the $-\underset{\underset{R^5}{|}}{C}=\underset{\underset{R^6}{|}}{C}-CO-NHR^2$ group is at the 1-position.

**Solvent code:
A, acetonitrile;
B, acetic acid;
C, ethyl acetate;
D, isopropanol/water;
E, ethanol;
F, isopropanol.

TABLE II
SPECTRAL DATA

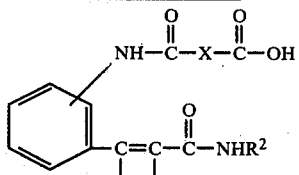

| R² | R⁵ | R⁶ | X | Position of NHCOXCOOH group* | IR (cm⁻¹) (KBr disc) | NMR (ppm) (DMSO-d₆) |
|---|---|---|---|---|---|---|
| octyl | H | H | —CH=CH— | 2 | 3333, 2941, 1724, 1664, 1550 | 0.82 (m, 3H), 1.27 (s, 12H), 3.15 (m, 2H), 6.55 (m, 4H) |
| octyl | H | H | —CH₂CH₂— | 2 | 3279, 2899, 1724, 1695, 1639, 1587 | 0.85 (m, 3H), 1.28 (s, 12H), 2.52 (m, 2H, under DMSO-d₆), 3.2 (m, 2H), 6.42 (s, 1H), 6.68 (s, 1H), 7.6 (m, 6H), 9.84 (s, 1H) |
| octyl | H | H | —CH₂CH₂CH₂— | 2 | 3279, 2899, 1739, 1667, 1613, 1538 | 0.89 (m, 3H), 1.25 (s, 12H), 1.90 (m, 2H), 2.35 (m, 4H, under DMSO-d₆), 3.18 (m, 2H), 6.4 (s, 1H), 6.69 (s, 1H), 7.75 (m, 6H), 9.8 (s, 1H) |
| octyl | H | H | —CH₂C(CH₃)₂CH₂— | 2 | 3226, 2941, 1739, 1667, 1613, 1538 | 0.89 (m, 3H), 1.12 (s, 6H), 1.27 (s, 12H), 2.45 (m, 4H, under DMSO-d₆), 3.17 (m, 2H), 6.41 (s, 1H), 6.66 (s, 1H), 7.72 (m, 6H), 9.78 (s, 1H) |
| decyl | H | H | —CH=CH— | 4 | 3279, 2942, 1724, 1667, 1639, 1550 | 0.92 (m, 3H), 1.23 (s, 16H), 3.18 (m, 2H), 6.49 (m, 4H), 7.80 (m, 6H), 10.58 (s, 1H) |
| decyl | H | H | —CH₂CH₂— | 4 | 3279, 2942, 1709, 1667, 1626, 1527 | 0.88 (m, 3H), 1.20 (s, 16H), 2.50 (m, 4H), 3.15 (m, 2H), 6.38 (s, 1H), 6.64 (s, 1H), 7.75 (m, 6H), 10.19 (s, 1H) |
| decyl | H | H | —CH₂C(CH₂)₂CH₂— | 4 | 3279, 2941, 1724, 1653, 1600, 1550 | 0.90 (m, 3H), 1.11 (s, 6H), 1.25 (s, 16H), 2.48 (m, 4H, under DMSO-d₆), 3.18 (m, 2H), 6.39 (s, 1H), 6.64 (s, 1H), 7.8 (m, 6H), 9.99 (s, 1H) |
| decyl | H | H | —CH₂CH₂— | 3 | 3226, 2899, 1709, 1667, 1626, 1550 | 0.89 (m, 3H), 1.23 (s, 16H), 2.51 (m, 4H), 3.18 (m, 2H), 6.44 (s, 1H), 6.70 (s, 1H), 7.75 (m, 6H), 9.68 (s, 1H) |
| decyl | H | H | —CH₂CH₂CH₂— | 3 | 3279, 2899, 1695, 1667, 1626, 1550 | 0.90 (m, 3H), 1.22 (s, 16H), 1.91 (m, 2H), 2.39 (m, 4H, under DMSO-d₆), 3.18 (m, 2H), 6.45 (s, 1H), 6.71 (s, 1H), 7.38 (m, 4H), 8.05 (m, 2H), 10.0 (s, 1H) |
| decyl | H | H | —CH=CH— | 2 | 3333, 2941, 1724, 1667, 1639, 1550 | 0.88 (m, 3H), 1.23 (s, 16H), 3.16 (m, 2H), 6.51 (m, 4H), 7.68 (m, 6H), 10.28 (s, 1H) |
| decyl | H | H | —CH₂CH₂— | 2 | 3333, 2941, 1739, 1724, 1653, 1538 | 0.89 (m, 3H), 1.25 (s, 16H), 2.50 (m, 4H, under DMSO-d₆), 3.17 (m, 2H), 6.42 (s, 1H), 6.69 (s, 1H), 7.62 (m, 6H), 9.8 (s, 1H) |
| decyl | H | H | —CH₂CH₂CH₂— | 2 | 3279, 2941, 1724, 1667, 1626, 1575 | 0.89 (m, 3H), 1.26 (s, 16H), 1.91 (m, 2H), 2.40 (m, 4H, under DMSO-d₆), 3.18 (m, 2H), 6.41 (s, 1H), 6.68 (s, 1H), 7.62 (m, 6H), 9.65 (s, 1H) |
| decyl | H | H | —CH₂C(CH₃)₂CH₂— | 2 | 3226, 2941, 1739, 1667, 1613, 1538 | 0.90 (m, 3H), 1.12 (s, 6H), 1.23 (s, 16H), 2.41 (m, 4H, under DMSO-d₆), 3.14 (m, 2H), 6.42 (s, 1H), 6.68 (s, 1H), 7.75 (m, 6H), 9.64 (s, 1H) |
| 1-methyldecyl | H | H | —CH=CH— | 4 | 3448, 3279, 2941, 1724, 1639, 1563 | 1.1 (m, 22H), 3.82 (m, 1H), 6.49 (m, 4H), 7.6 (m, 6H), 10.48 (s, 1H) |
| 1-methyldecyl | H | H | —CH₂CH₂— | 4 | 3333, 2941, 1695, 1667, 1613, 1538 | 0.91 (m, 3H), 1.19 (m, 19H), 2.52 (m, 4H, under DMSO-d₆), 3.89 (m, 1H), 6.37 (s, 1H), 6.63 (s, 1H), 7.62 (m, 6H), 10.1 (s, 1H) |
| 1-methyldecyl | H | H | —CH₂CH₂CH₂— | 4 | 3226, 2899, 1709, 1667, 1626, 1527 | 0.89 (m, 3H), 1.18 (m, 19H), 1.89 (m, 2H), 2.40 (m, 4H, |

TABLE II-continued
SPECTRAL DATA $$\underset{\underset{R^5\ R^6}{\overset{|\ \ \ |}{\underset{\text{Position of}}{C=C-\overset{O}{\overset{\|}{C}}-NHR^2}}}}{\overset{NH-\overset{O}{\overset{\|}{C}}-X-\overset{O}{\overset{\|}{C}}-OH}{\bigcirc}}$$

| R² | R⁵ | R⁶ | X | Position of NHCOXCOOH group* | IR (cm⁻¹) (KBr disc) | NMR (ppm) (DMSO-d₆) |
|---|---|---|---|---|---|---|
| | | | | | | under DMSO-d₆), 3.88 (m, 1H), 6.39 (s, 1H), 6.65 (s, 1H), 7.60 (m, 6H), 10.04 (s, 1H) |
| 1-methyldecyl | H | H | —CH₂C(CH₃)₂CH₂— | 4 | 3279, 2899, 2667, | 0.84 (m, 3H), 1.10 (m, 27H), 2.40 (m, 4H, under DMSO-d₆), 3.75 (m, 1H), 6.32 (s, 1H), 6.60 (s, 1H), 7.55 (m, 6H), 9.90 (s, 1H) |
| 1-methyldecyl | H | H | —CH=CH— | 3 | 3226, 2899, 1724, 1653, 1626, 1587 | 0.90 (m, 3H), 1.18 (m, 19H), 3.85 (m, 1H), 6.50 (m, 4H), 7.39 (m, 4H), 8.05 (m, 2H), 10.14 (s, 1H) |
| 1-methyldecyl | H | H | —CH₂CH₂— | 3 | 3279, 2941, 1802, 1724, 1681, 1639 | 0.89 (m, 3H), 1.20 (m, 19H), 2.55 (m, 4H, under DMSO-d₆), 3.83 (m, 1H), 6.46 (s, 1H), 6.74 (s, 1H), 7.39 (m, 4H), 7.99 (m, 2H), 10.02 (m, 2H) |
| 1-methyldecyl | H | H | —CH₂CH₂CH₂— | 3 | 3279, 2899, 1709, 1653, 1626, 1527 | 0.89 (m, 3H), 1.21 (m, 19H), 1.89 (m, 2H), 2.40 (m, 4H, under DMSO-d₆), 3.90 (m, 1H), 6.48 (s, 1H), 6.75 (s, 1H), 7.36 (m, 4H), 7.97 (m, 2H), 9.94 (s, 1H) |
| 1-methyldecyl | H | H | —CH=CH— | 2 | 3333, 2941, 1724, 1667, 1626, 1538 | 0.90 (m, 3H), 1.19 (m, 19H), 3.82 (m, 1H), 6.52 (m, 4H), 7.58 (m, 6H), 10.34 (s, 1H) |
| 1-methyldecyl | H | H | —CH₂CH₂— | 2 | 3333, 2941, 1739, 1709, 1653, 1600 | 0.89 (m, 3H), 1.20 (m, 19H), 2.48 (m, 4H, under DMSO-d₆), 3.70 (m, 1H), 6.41 (s, 1H), 6.68 (s, 1H), 7.55 (m, 6H), 9.76 (s, 1H) |
| 1-methyldecyl | H | H | —CH₂CH₂CH₂— | 2 | 3226, 2899, 1739, 1667, 1600, 1538 | 0.89 (m, 3H), 1.21 (m, 19H), 1.88 (m, 2H), 2.40 (m, 4H, under DMSO-d₆), 3.85 (m, 1H), 6.42 (s, 1H), 6.68 (s, 1H), 7.54 (m, 6H), 9.64 (s, 1H) |
| 1-methyldecyl | H | H | —CH₂C(CH₃)CH₂— | 2 | 3279, 2899, 1739, 1667, 1613, 1538 | 0.90 (m, 3H), 1.18 (m, 25H), 2.45 (m, 4H, under DMSO-d₆), 3.89 (m, 1H), 6.43 (s, 1H), 6.70 (s, 1H), 7.55 (m, 6H), 9.74 (s, 1H) |
| cycloheptyl | H | H | —CH=CH— | 4 | 3279, 2941, 1724, 1667, 1600, 1550 | 1.50 (s, 12H), 4.65 (m, 1H), 6.42 (m, 4H), 7.65 (m, 6H), 10.54 (s, 1H) |
| cycloheptyl | H | H | —CH=CH— | 3 | 3333, 2941, 1739, 1667, 1613, 1575 | 1.50 (s, 12H), 3.75 (m, 1H), 6.52 (m, 4H), 7.38 (m, 4H), 8.12 (m, 2H), 10.56 (s, 1H) |
| cycloheptyl | H | H | —CH₂CH₂— | 3 | 3448, 3333, 2941, 1709, 1639, 1613 | 1.51 (s, 12H), 2.57 (m, 4H, under DMSO-d₆), 3.81 (m, 1H), 6.51 (s, 1H), 6.79 (s, 1H), 7.35 (m, 4H), 8.12 (m, 2H), 10.16 (s, 1H) |
| cycloheptyl | H | H | —CH₂CH₂CH₂— | 3 | 3448, 3333, 2941, 1709, 1667, 1550 | 1.49 (s, 12H), 1.90 (m, 2H), 2.41 (m, 4H, under DMSO-d₆), 3.85 (m, 1H), 6.46 (s, 1H), 6.72 (s, 1H), 7.38 (m, 4H), 8.04 (m, 2H), 10.04 (s, 1H) |
| cycloheptyl | H | H | —CH₂C(CH₃)₂CH₂— | 3 | 3333, 2941, 1709, 1667, 1639, 1563 | 1.08 (s, 6H), 1.52 (s, 12H), 2.42 (m, 4H, under DMSO-d₆), 3.88 (m, 1H), 6.46 (s, 1H), 6.72 (s, 1H), 7.45 (m, 4H), 8.04 (m, 2H), 9.88 (s, 1H) |
| cyclodecyl | H | H | —CH=CH— | 4 | 3279, 2941, 1724, 1667, 1600, 1550 | 1.39 (s, 22H), 4.22 (m, 1H), 6.65 (m, 4H), 7.39 (m, 4H) (CF₃COOD used as solvent) |
| cyclodecyl | H | H | —CH₂CH₂— | 4 | 3390, 2985, 1724, 1695, 1667, 1600 | 1.38 (s, 22H), 2.60 (m, 4H, under DMSO-d₆), 4.09 (m, 1H), |

TABLE II-continued

SPECTRAL DATA

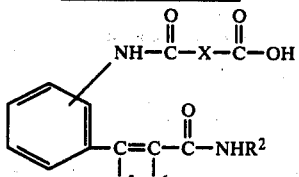

| $R^2$ | $R^5$ | $R^6$ | X | Position of NHCOXCOOH group* | IR (cm$^{-1}$) (KBr disc) | NMR (ppm) (DMSO-$d_6$) |
|---|---|---|---|---|---|---|
| cyclodecyl | H | H | $-CH_2C(CH_3)_2CH_2-$ | 4 | 3333, 2941, 1754, 1667, 1613, 1550 | 6.45 (s, 1H), 6.72 (s, 1H), 7.60 (m, 6H), 10.06 (s, 1H) 1.03 (s, 6H), 1.25 (s, 22H), 2.39 (m, 4H, under DMSO-$d_6$), 3.82 (m, 1H), 6.17 (s, 1H), 6.42 (s, 1H), 7.29 (m, 6H), 9.56 (s, 1H) |
| cyclodecyl | H | H | $-CH=CH-$ | 3 | 3279, 2941, 1724, 1667, 1639, 1550 | 1.32 (s, 22H), 4.00 (m, 1H), 6.55 (m, 4H), 7.38 (m, 4H), 7.96 (m, 2H), 10.44 (s, 1H) |
| cyclodecyl | H | H | $-CH_2CH_2CH_2-$ | 3 | 3333, 2941, 1739, 1667, 1639, 1538 | 1.31 (s, 22H), 1.88 (m, 2H), 2.36 (m, 4H, under DMSO-$d_6$), 3.99 (m, 1H), 6.46 (s, 1H), 6.73 (s, 1H), 7.36 (m, 4H), 7.95 (m, 2H), 9.90 (s, 1H) |
| octyl | H | $CH_3$ | $-CH=CH-$ | 4 | 3333, 2941, 1739, 1639, 1613, 1527 | |
| octyl | H | $CH_3$ | $-CH=CH-$ | 3 | 3279, 2899, 1724, 1626, 1587, 1538 | |
| octyl | H | $CH_3$ | $-CH_2CH_2CH_2-$ | 3 | 3333, 2941, 1724, 1667, 1613, 1529 | |
| decyl | H | $CH_3$ | $-CH=CH-$ | 4 | 3390, 2985, 1739, 1639, 1626, 1538 | |
| decyl | H | $CH_3$ | $-CH_2CH_2-$ | 4 | 3333, 2941, 1709, 1667, 1626, 1538 | |
| decyl | H | $CH_3$ | $-CH=CH-$ | 3 | 3279, 2899, 1709, 1626, 1587, 1550 | |
| decyl | H | $CH_3$ | $-CH_2CH_2-$ | 3 | 3226, 2899, 1724, 1681, 1587, 1550 | |
| decyl | H | $CH_3$ | $-CH_2CH_2CH_2-$ | 3 | 3333, 2899, 1724, 1681, 1613, 1527 | |
| 1-methyldecyl | H | $CH_3$ | $-CH=CH-$ | 4 | 3333, 2941, 1739, 1639, 1613, 1538 | |
| 1-methyldecyl | H | $CH_3$ | $-CH=CH-$ | 3 | 3279, 2899, 1709, 1626, 1587, 1550 | |
| cycloheptyl | H | $CH_3$ | $-CH=CH-$ | 4 | 3077, 2941, 1709, 1639, 1587, 1515 | |
| cycloheptyl | H | $CH_3$ | $-CH_2CH_2-$ | 4 | 3390, 2941, 1739, 1653, 1613, 1538 | |
| decyl | $CH_3$ | H | $-CH=CH-$ | 4 | 3333, 2941, 1739, 1639, 1550, 1504 | 0.91 (m, 3H), 1.25 (s, 16H), 2.47 (s, 3H, under DMSO-$d_6$), 3.16 (m, 2H), 6.37 (m, 3H), 7.65 (m, 6H), 10.48 (s, 1H) |
| decyl | $CH_3$ | H | $-CH_2CH_2CH_2-$ | 4 | 3333, 2941, 1739, 1667, 1653, 1538 | 0.90 (m, 3H), 1.25 (s, 16H), 1.89 (m, 2H), 2.38 (m, 7H, under DMSO-$d_6$), 3.11 (m, 2H), 6.22 (s, 1H), 7.60 (m, 6H), 10.00 (s, 1H) |
| 1-methyldecyl | $CH_3$ | H | $-CH=CH-$ | 4 | 3333, 2941, 1724, 1639, 1600, 1550 | 0.89 (m, 3H), 1.08 (m, 3H), 1.21 (s, 16H), 2.45 (m, 3H, under DMSO-$d_6$), 3.80 (m, 1H), 6.35 (m, 3H), 7.58 (m, 6H), 10.54 (s, 1H) |
| 1-methyldecyl | $CH_3$ | H | $-CH_2CH_2CH_2-$ | 4 | 3279, 2899, 1695, 1653, 1639, 1527 | 0.89 (m, 3H), 1.08 (m, 3H), 1.22 (s, 16H), 1.88 (m, 2H), 2.41 (m, 7H, under DMSO-$d_6$), 3.78 (m, 1H), 6.21 (s, 1H), 7.63 (m, 6H), 9.98 (s, 1H) |

*The numeral in this column indicates the position of the NHCOXCOOH group on the phenyl ring; the $-\underset{R^5}{C}=\underset{R^6}{C}-CO-NHR^2$ group is at the 1-position.

EXAMPLE 3

The appropriate product from Preparation 24, 25 or 26 is heated with maleic anhydride, succinic anhydride, glutaric anhydride, 3-methylglutaric anhydride or 3,3- dimethylglutaric anhydride, according to the procedure of Example 1. This affords the following compounds:

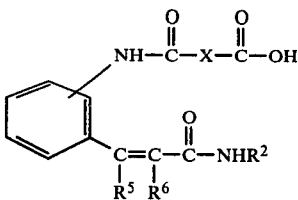

| R² | R⁵ | R⁶ | X | Position of NHCOXCOOH group* |
|---|---|---|---|---|
| octyl | H | H | —CH=CH— | 4 |
| octyl | H | H | —CH₂CH₂— | 3 |
| 1-methylheptyl | H | H | —CH₂CH₂CH₂— | 4 |
| 1-methylheptyl | H | H | —CH₂CH(CH₃)CH₂— | 3 |
| 6-methylheptyl | H | H | —CH₂C(CH₃)₂CH₂— | 2 |
| 1-pentylhexyl | H | H | —CH=CH— | 2 |
| pentadecyl | H | H | —CH₂CH₂CH₂— | 3 |
| pentadecyl | H | H | —CH₂CH(CH₃)CH₂— | 4 |
| 2-methyltetradecyl | H | H | —CH₂C(CH₃)₂CH₂— | 3 |
| cyclohexyl | H | H | —CH=CH— | 4 |
| cyclohexyl | H | H | —CH₂CH₂— | 3 |
| nonyl | H | CH₃ | —CH₂CH₂CH₂— | 2 |
| pentadecyl | H | CH₃ | —CH₂CH(CH₃)CH₂— | 4 |
| cyclohexyl | H | CH₃ | —CH₂C(CH₃)₂CH₂— | 3 |
| cyclododecyl | H | CH₃ | —CH=CH— | 4 |
| octyl | CH₃ | H | —CH₂CH₂— | 2 |
| 1-methyldecyl | CH₃ | H | —CH₂CH(CH₃)CH₂— | 3 |
| tridecyl | CH₃ | H | —CH₂CH(CH₃)CH₂— | 3 |
| pentadecyl | CH₃ | H | —CH₂C(CH₃)₂CH₂— | 4 |
| cyclohexyl | CH₃ | H | —CH=CH— | 4 |
| cyclodecyl | CH₃ | H | —CH₂CH₂— | 2 |
| cyclododecyl | CH₃ | H | —CH₂CH₂CH₂— | 3 |
| octyl | CH₃ | CH₃ | —CH₂CH(CH₃)CH₂— | 2 |
| 1-methylnonyl | CH₃ | CH₃ | —CH₂C(CH₃)₂CH₂— | 3 |
| tridecyl | CH₃ | CH₃ | —CH=CH— | 4 |
| pentadecyl | CH₃ | CH₃ | —CH₂CH₂— | 3 |
| cyclohexyl | CH₃ | CH₃ | —CH₂CH₂CH₂— | 4 |
| cyclononyl | CH₃ | CH₃ | —CH₂CH(CH₃)CH₂— | 2 |
| cycloundecyl | CH₃ | CH₃ | —CH₂C(CH₃)₂CH₂— | 3 |
| cyclododecyl | CH₃ | CH₃ | —CH=CH— | 4 |

*The numeral in this column indicates the position of the NHCOXCOOH group on the phenyl ring; the —C=C—CO—NHR² group is at the 1-position.

EXAMPLE 4

N-(1-Methyldecyl)-3-(3-[cis-3-carboxypropenamido]-phenyl)-2-butenamide

A stirred solution of 1.0 g. of the N-(1-methyldecyl)-3-(3-aminophenyl)-2-butenamide from Preparation 27 in 25 ml. of toluene was heated on a steam bath, and then 0.32 g. of maleic anhydride was added in one portion. After a few minutes the reaction mixture was cooled and the toluene was removed by evaporation in vacuo. The residue was recrystallized from acetonitrile to give 0.70 g. of the title compound as a white solid, m.p. 76°–78° C. (dec.). The IR spectrum (KBr disc) showed absorptions at 3448, 3279, 2941, 1724, 1639, 1587 and 1563 cm⁻¹. The NMR spectrum (DMSO-d₆) showed absorptions at 0.9 (m, 3H), 1.09 (m, 3H), 1.26 (s, 16H), 2.47 (m, 3H, under DMSO-d₆), 3.8 (m, 1H), 6.26 (m, 3H), 7.62 (m, 6H) and 10.44 (s, 1H) ppm.

Analysis: Calcd. for C₂₅H₃₆N₂O₄: C, 70.06; H, 8.47; N, 6.53%. Found: C, 69.95; H, 8.28; N, 6.54%.

EXAMPLE 5

N-(1-Methyldecyl)-3-(3-[cis-3-carboxypropenamido]-phenyl)-2-butenamide

A stirred solution of 1.0 g. of the N-(1-methyldecyl)-3-(3-aminophenyl)-2-butenamide from Preparation 28 in 25 ml. of toluene was heated on a steam bath, and then 0.32 g. of maleic anhydride was added in one portion. After 3 minutes, the reaction mixture was cooled and the solvent was removed by evaporation in vacuo. The residue was triturated under a mixture of petroleum ether and acetonitrile, and the resulting solid was recrystallized from acetonitrile. This afforded 0.68 g. of the title compound as a light yellow solid, m.p. 126°–128° C. The IR spectrum (KBr disc) showed absorptions at 3333, 2941, 1724, 1639, 1587 and 1563 cm⁻¹. The NMR spectrum (DMSO-d₆) showed absorptions at 0.81 (s, 3H), 0.91 (s, 3H), 1.17 (s, 16H), 2.02 (m, 3H), 3.58 (m, 1H), 5.90 (d, 1H), 6.38 (m, 2H), 7.26 (m, 6H) and 10.40 (s, 1H) ppm.

Analysis: Calcd. for C₂₅H₃₆N₂O₄: C, 70.06; H, 8.47; N, 6.53%. Found: C, 70.28; H, 8.19; N, 6.57%.

EXAMPLE 6

N-(1-Methyldecyl)-3-(3-[4-carboxybutanamido]-phenyl)-2-butenamide

A stirred solution of 0.61 g. of N-(1-methyldecyl)-3-(3-aminophenyl)-2-butenamide, prepared in a manner analogous to Preparation 27, in 25 ml. of toluene, was heated on a steam bath and then 0.23 g. of glutaric anhydride was added in one portion. After 5 minutes, the reaction mixture was cooled and the solvent was removed by evaporation in vacuo. The residue was recrystallized twice from acetonitrile, to give 370 mg. of the title compound, m.p. 136°–140° C. This latter material was recrystallized from isopropanol/water to give 196 mg. of material having a melting point of 140°–141.5° C. The IR spectrum (KBr disc) showed absorptions at 3390, 2895, 1724, 1681, 1613 and 1575 cm$^{-1}$. The NMR spectrum (DMSO-d$_6$) showed absorptions at 0.90 (m, 3H), 1.08 (m, 3H), 1.26 (s, 16H), 1.89 (m, 2H), 2.40 (m, 7H, under DMSO-d$_6$), 3.80 (m, 1H), 6.19 (s, 1H), 7.51 (m, 6H) and 9.90 (s, 1H) ppm.

Analysis: Calcd. for $C_{26}H_{40}N_2O_4$: C, 70.24; H, 9.07; N, 6.30%. Found: C, 69.80; H, 9.05; N, 6.19%.

EXAMPLE 7

N-(1-Methyldecyl)-3-(3-[4-carboxybutanamido]-phenyl)-2-butenamide

A stirred solution of 0.83 g. of the N-(1-methyldecyl)-3-(3-aminophenyl)-2-butenamide from Preparation 28 in 25 ml. of toluene was heated on a steam bath, and 0.31 g. of glutaric anhydride was added in one portion. After 5 minutes, the solution was concentrated in vacuo, which caused a gum to form. The remaining toluene was poured off, and the residue was induced to solidify by trituration under petroleum ether. The solid was recrystallized three times from acetonitrile, giving 261 mg. of the title compound, m.p. 115°–117.5° C. The IR spectrum (KBr disc) showed absorptions at 3279, 2941, 1709, 1667, 1639, 1600 and 1550 cm$^{-1}$. The NMR spectrum (DMSO-d$_6$) showed absorptions at 0.82 (m, 3H), 0.94 (m, 3H), 1.21 (s, 16H), 1.85 (m, 2H), 2.05 (m, 3H), 2.32 (m, 4H, under DMSO-d$_6$), 3.60 (m, 1H), 5.89 (d, 1H), 7.20 (m, 6H) and 9.80 (s, 1H) ppm.

Analysis: Calcd. for $C_{26}H_{40}N_2O_4$: C, 70.24; H, 9.07; N, 6.30%. Found: C, 70.24; H, 9.06; N, 6.36%.

EXAMPLE 8

N-Decyl-3-(3-[cis-3-methoxycarbonylpropenamido]-phenyl)propenamide

To a stirred mixture of 400 mg. of N-decyl-3-(3-[cis-3-carboxypropenamido]phenyl)propenamide and 15 ml. of 1,2-dimethoxyethane is added a solution of 1.5 mmoles of diazomethane in 5 ml. of ether. The reaction mixture is stirred at room temperature for 16 hours, and then the excess diazomethane is decomposed by the addition of a few drops of acetic acid. The total solvents are removed by evaporation in vacuo, and the residue is dissolved in ethyl acetate. The ethyl acetate solution is washed with 1 N sodium hydroxide, followed by water, followed by saturated sodium chloride solution, and then dried using sodium sulfate. Evaporation of the dried ethyl acetate solution in vacuo affords the title compound.

EXAMPLE 9

By esterification of the appropriate product from Examples 2 and 3 with the requisite diazoalkane, using the procedure of Example 8, the following compounds can be prepared:

| R$^1$ | R$^2$ | R$^5$ | R$^6$ | X | Position of NHCOXCOOR$^1$ group* |
|---|---|---|---|---|---|
| methyl | octyl | H | H | —CH=CH— | 2 |
| ethyl | octyl | H | H | —CH$_2$CH$_2$CH$_2$— | 4 |
| propyl | decyl | H | H | —CH$_2$C(CH$_3$)$_2$CH$_2$— | 4 |
| butyl | 1-pentahexyl | H | H | —CH=CH— | 2 |
| methyl | pentadecyl | H | H | —CH$_2$CH$_2$CH$_2$— | 3 |
| ethyl | cyclohexyl | H | H | —CH$_2$CH$_2$— | 3 |
| methyl | cycloheptyl | H | H | —CH=CH— | 4 |
| methyl | cyclododecyl | H | H | —CH$_2$CH$_2$— | 4 |
| butyl | cyclododecyl | H | H | —CH$_2$C(CH$_3$)$_2$CH$_2$— | 4 |
| methyl | octyl | H | CH$_3$ | —CH=CH— | 3 |
| ethyl | nonyl | H | CH$_3$ | —CH$_2$CH$_2$CH$_2$— | 2 |
| propyl | decyl | H | CH$_3$ | —CH$_2$CH$_2$— | 3 |
| methyl | 1-methyldecyl | H | CH$_3$ | —CH=CH— | 3 |
| methyl | pentadecyl | H | CH$_3$ | —CH$_2$CH(CH$_3$)CH$_2$— | 4 |
| ethyl | cyclohexyl | H | CH$_3$ | —CH$_2$C(CH$_3$)$_2$CH$_2$— | 3 |
| butyl | cycloheptyl | H | CH$_3$ | —CH=CH— | 4 |
| methyl | cyclododecyl | H | CH$_3$ | —CH=CH— | 4 |
| ethyl | octyl | CH$_3$ | H | —CH$_2$CH$_2$— | 2 |
| methyl | decyl | CH$_3$ | H | —CH=CH— | 4 |
| butyl | 1-methyldecyl | CH$_3$ | H | —CH$_2$CH(CH$_3$)CH$_2$— | 3 |
| methyl | tridecyl | CH$_3$ | H | —CH$_2$CH(CH$_3$)CH$_2$— | 3 |
| ethyl | pentadecyl | CH$_3$ | H | —CH$_2$C(CH$_3$)$_2$CH$_2$— | 4 |
| methyl | cyclohexyl | CH$_3$ | H | —CH=CH— | 4 |
| propyl | cyclodecyl | CH$_3$ | H | —CH$_2$CH$_2$— | 2 |

-continued

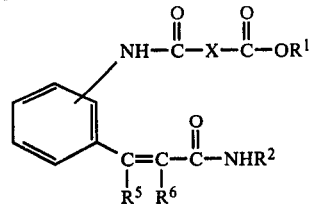

| R[1] | R[2] | R[5] | R[6] | X | Position of NHCOXCOOR[1] group* |
|---|---|---|---|---|---|
| methyl | cyclododecyl | CH$_3$ | H | —CH$_2$CH$_2$CH$_2$— | 3 |
| ethyl | octyl | CH$_3$ | CH$_3$ | —CH$_2$CH(CH$_3$)CH$_2$— | 2 |
| methyl | 1-methylnonyl | CH$_3$ | CH$_3$ | —CH$_2$C(CH$_3$)$_2$CH$_2$— | 3 |
| butyl | tridecyl | CH$_3$ | CH$_3$ | —CH=CH— | 4 |
| methyl | pentadecyl | CH$_3$ | CH$_3$ | —CH$_2$CH$_2$— | 3 |
| propyl | cyclohexyl | CH$_3$ | CH$_3$ | —CH$_3$CH$_2$CH$_2$— | 4 |
| methyl | cyclononyl | CH$_3$ | CH$_3$ | —CH$_2$CH(CH$_3$)CH$_2$— | 2 |
| ethyl | cycloundecyl | CH$_3$ | CH$_3$ | —CH$_2$C(CH$_3$)$_2$CH$_2$— | 3 |
| methyl | cyclododecyl | CH$_3$ | CH$_3$ | —CH=CH— | 4 |

*The numeral in this column indicates the position of the NHCOXCOOR[1] group on the phenyl ring; the —C=C—CO—NHR[2] group is at the 1-position.
  | |
  R[5] R[6]

EXAMPLE 10

N-Decyl-3-(3-[cis-3-(2-[N,N-diethylamino]ethoxycarbonyl)propenamido]phenyl)propenamide To a stirred solution of 800 mg. of N-decyl-3-(3-[cis-3-carboxypropenamido]phenyl)propenamide in 25 ml. of tetrahydrofuran is added 357 mg. of carbonyldiimidazole. The mixture is heated under reflux for 10 minutes, and then 258 mg. of 2-(N,N-diethylamino)ethanol is added. The mixture is again heated under reflux for 10 minutes, and then an additional 258 mg. of 2-(N,N-diethylamino)ethanol is added. The mixture is heated under reflux for 15 minutes and then it is cooled to room temperature. The solvent is removed by evaporation in vacuo, and the residue is dissolved in 75 ml. of ethyl acetate. The ethyl acetate solution is washed successively with water, 1 N sodium hydroxide, water and saturated sodium chloride solution. The ethyl acetate solution is then dried and evaporated in vacuo to give the title compound.

EXAMPLE 11

By esterification of the requisite product from Example 1 or 2 with the appropriate 2-(N,N-dialkylamino)ethanol and carbonyldiimidazole, using the procedure of Example 10, the following compounds can be prepared:

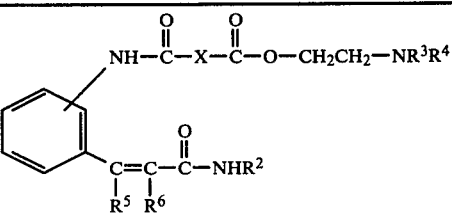

| R[2] | R[3] | R[4] | R[5] | R[6] | X | Position of NHCOXCOO—CH$_2$CH$_2$NR[3]—R[4] group* |
|---|---|---|---|---|---|---|
| octyl | methyl | methyl | H | H | —CH=CH— | 2 |
| octyl | ethyl | ethyl | H | H | —CH$_2$CH$_2$CH$_2$— | 4 |
| decyl | propyl | propyl | H | H | —CH$_2$C(CH$_3$)$_2$CH$_2$— | 4 |
| 1-pentylhexyl | isopropyl | isopropyl | H | H | —CH=CH— | 2 |
| pentadecyl | methyl | ethyl | H | H | —CH$_2$CH$_2$CH$_2$— | 3 |
| cyclohexyl | methyl | methyl | H | H | —CH$_2$CH$_2$— | 3 |
| cycloheptyl | ethyl | ethyl | H | H | —CH=CH— | 4 |
| cyclododecyl | ethyl | isopropyl | H | H | —CH$_2$CH$_2$— | 4 |
| cyclodecyl | ethyl | ethyl | H | H | —CH$_2$C(CH$_3$)$_2$CH$_2$— | 4 |
| octyl | isopropyl | methyl | H | CH$_3$ | —CH=CH— | 3 |
| nonyl | methyl | methyl | H | CH$_3$ | —CH$_2$CH$_2$CH$_2$— | 2 |
| decyl | ethyl | ethyl | H | CH$_3$ | —CH$_2$CH$_2$— | 3 |
| 1-methyl- | | | | | | |

-continued

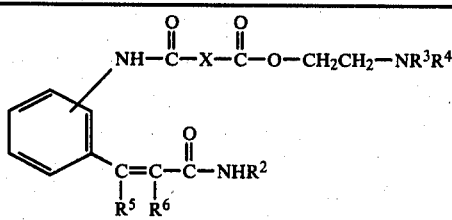

| R² | R³ | R⁴ | R⁵ | R⁶ | X | Position of NHCOXCOO—CH₂CH₂NR³—R⁴ group* |
|---|---|---|---|---|---|---|
| decyl | propyl | methyl | H | CH₃ | —CH=CH— | 3 |
| pentadecyl | methyl | methyl | H | CH₃ | —CH₂CH(CH₃)CH₂— | 4 |
| cyclohexyl | ethyl | ethyl | H | CH₃ | —CH₂C(CH₃)₂CH₂— | 3 |
| cycloheptyl | ethyl | propyl | H | CH₃ | —CH=CH— | 4 |
| cyclododecyl | ethyl | ethyl | H | CH₃ | —CH=CH— | 4 |
| octyl | isopropyl | isopropyl | CH₃ | H | —CH₂CH₂— | 2 |
| decyl | methyl | methyl | CH₃ | H | —CH=CH— | 4 |
| 1-methyldecyl | ethyl | ethyl | CH₃ | H | —CH₂CH(CH₃)CH₂— | 3 |
| tridecyl | propyl | propyl | CH₃ | H | —CH₂CH(CH₃)CH₂— | 3 |
| pentadecyl | propyl | methyl | CH₃ | H | —CH₂C(CH₃)₂CH₂— | 4 |
| cyclohexyl | ethyl | ethyl | CH₃ | H | —CH=CH— | 4 |
| cyclodecyl | methyl | methyl | CH₃ | H | —CH₂CH₂— | 2 |
| cyclododecyl | methyl | ethyl | CH₃ | H | —CH₂CH₂CH₂— | 3 |
| octyl | methyl | propyl | CH₃ | CH₃ | —CH₂CH(CH₃)CH₂— | 2 |
| 1-methylnonyl | methyl | isopropyl | CH₃ | CH₃ | —CH₂C(CH₃)₂CH₂— | 3 |
| tridecyl | ethyl | methyl | CH₃ | CH₃ | —CH=CH— | 4 |
| pentadecyl | propyl | ethyl | CH₃ | CH₃ | —CH₂CH₂— | 3 |
| cyclohexyl | isopropyl | propyl | CH₃ | CH₃ | —CH₂CH₂CH₂— | 4 |
| cyclononyl | ethyl | isopropyl | CH₃ | CH₃ | —CH₂CH(CH₃)CH₂— | 2 |
| cycloundecyl | methyl | methyl | CH₃ | CH₃ | —CH₂C(CH₃)₂CH₂— | 3 |
| cyclododecyl | ethyl | ethyl | CH₃ | CH₃ | —CH=CH— | 4 |

*The numeral in this column indicates the position of the NHCOXCOOCH₂CH₂NR³R⁴ group on the phenyl ring; the —C=C—CO—NHR² group is at the 1-position.

PREPARATION 1

Ethyl 3-(4-Nitrophenyl)-2-butenoate

A 50% suspension of sodium hydride in mineral oil (10.7 g.) was washed with petroleum ether to remove the mineral oil, and then the residue was suspended in 330 ml. of 1,2-dimethoxyethane, under nitrogen. To this suspension was added, dropwise, during 45 minutes, 52.5 g. of diethyl ethoxycarbonyl-methylphosphonate. After the evolution of gas had ceased, a solution of 35.0 g. of 4-nitroacetophenone in 200 ml. of 1,2-dimethoxyethane was added during 50 minutes. The resulting mixture was stirred overnight, and then the solvent was removed by evaporation in vacuo. The residue was partitioned between ethyl acetate and water, and then the ethyl acetate layer was removed. The ethyl acetate layer was dried using sodium sulfate and then it was evaporated in vacuo. This afforded an oil which was induced to solidify by scratching. The solid was recrystallized from ethanol to give 16.6 g. (33% yield) of the title product, m.p. 71°–74° C.

PREPARATION 2

Ethyl 3-(2-Nitrophenyl)-2-butenoate

The procedure of Preparation 1 is repeated, except that the 4-nitroacetophenone replaced by an equal weight of 2-nitroacetophenone. This affords the title compound.

PREPARATION 3

Reaction of 2-nitroacetophenone, 3-nitroacetophenone and 4-nitroacetophenone with diethyl 1-(ethoxycarbonyl)ethylphosphonate, according to the procedure of Preparation 1, affords:
  ethyl 2-methyl-3-(2-nitrophenyl)-2-butenoate,
  ethyl 2-methyl-3-(3-nitrophenyl)-2-butenoate and
  ethyl 2-methyl-3-(4-nitrophenyl)-2-butenoate, respectively.

PREPARATION 4

Ethyl 3-(3-Nitrophenyl)-2-butenoate

A 50% suspension of sodium hydride in mineral oil (28.32 g.) was washed with petroleum ether to remove the mineral oil, and then the residue was suspended in 500 ml. of 1,2-dimethoxyethane under nitrogen. To this suspension was added dropwise, with stirring, 139.5 g. of diethyl ethoxycarbonylmethylphosphonate, during 50 minutes. After gas evolution had ceased, a solution of 92.5 g. of 3-nitroacetophenone in 300 ml. of 1,2-dimethoxyethane was added during 90 minutes. The reaction mixture was stirred overnight, and then the solvent was removed by evaporation in vacuo. The residue was partitioned between ethyl acetate and water, and then the ethyl acetate layer was removed. The ethyl acetate layer was washed with saturated sodium chloride solution and dried using sodium sulfate. Evaporation in vacuo afforded an oil, which was chromatographed on ca. 400 g. of silica gel, using 2:1 hexane-ethyl acetate as eluant. The product-containing fractions were combined and evaporated, giving 124.5 g. of the title compound.

PREPARATION 5

Ethyl 2-Methyl-3-(3-Nitrophenyl)propenoate

To a stirred slurry of 79.8 g. of triphenyl(1-[ethoxycarbonyl]ethylidene)phosphorane in 300 ml. of benzene was added 30.2 g. of 3-nitrobenzaldehyde and the resulting mixture was heated under reflux overnight. The reaction mixture was cooled and the solvent was removed by evaporation in vacuo. The residue was extracted with 300 ml. of isopropyl ether. The isopropyl ether solution was filtered, and the filtrate was evaporated in vacuo. The residue was distilled under reduced pressure, giving 37.6 g. of the title product, b.p. 147°-162° C./0.25 mm Hg. The NMR spectrum (in $CDCl_3$) showed absorptions at 1.4 (t), 2.1 (d), 4.3 (q), 7.4 (m) and 8.1 (m) ppm.

PREPARATION 6

Ethyl 2-Methyl-3-(4-Nitrophenyl)propenoate

The title compound was prepared from triphenyl(1-[ethoxycarbonyl]ethylidene)phosphorane and 4-nitrobenzaldehyde, substantially according to Preparation 5. The product was obtained in 56% yield, as an orange-yellow solid, m.p. 70.5°-73° C.

PREPARATION 7

Ethyl 2-Methyl-3-(2-Nitrophenyl)propenoate

The title compound is prepared from triphenyl(1-[ethoxycarbonyl]ethylidene)phosphorane and 2-nitrobenzaldehyde, using the procedure of Preparation 5.

PREPARATION 8

3-(4-Nitrophenyl)-2-butenoic Acid

A mixture of 16.6 g. of ethyl 3-(4-nitrophenyl)-2-butenoate, 75 ml. of ethanol and 94.7 ml. of 1.5 N potassium hydroxide was heated on a steam bath for 70 minutes, and then it was cooled to room temperature. To the reaction mixture was added 200 ml. of water and 200 ml. of ethyl acetate. The aqueous phase was recovered and acidified with concentrated hydrochloric acid, and then the solid was recovered by filtration. This latter solid was recrystallized from aqueous ethanol to give 9.8 g. (67% yield) of the title compound, m.p. 167°-169° C.

PREPARATION 9

2-Methyl-3-(4-Nitrophenyl)propenoic Acid

The title compound was prepared in 60% yield by hydrolysis of its ethyl ester, according to the procedure of Preparation 8. Melting point: 201°-203° C. (dec.).

PREPARATION 10

2-Methyl-3-(3-Nitrophenyl)propenoic Acid

The title compound was prepared in 100% yield by hydrolysis of its ethyl ester substantially according to the procedure of Preparation 8. Melting point: 201°-202° C.

PREPARATION 11

By hydrolysis of the corresponding ethyl ester, according to the procedure of Preparation 8, the following compounds are prepared:
3-(2-nitrophenyl)-2-butenoic acid,
2-methyl-3-(2-nitrophenyl)-2-butenoic acid,
2-methyl-3-(3-nitrophenyl)-2-butenoic acid,
2-methyl-3-(4-nitrophenyl)-2-butenoic acid and
2-methyl-3-(2-nitrophenyl)propenoic acid.

PREPARATION 12

3-(3-Nitrophenyl)-2-butenoic Acid

A stirred mixture of 119.5 g. of ethyl 3-(3-nitrophenyl)-2-butenoate (from Preparation 4), 100 ml. of ethanol and 1,500 ml. of 1 N potassium hydroxide was heated on a steam bath for 1.25 hours. The reaction was cooled and then acidified with concentrated hydrochloric acid. The solid which precipitated was recovered by filtration (92.6 g.).

A portion (76.9 g.) of the above crude product was recrystallized from isopropanol, giving 48.9 g. of the title product, m.p. 208°-210° C. In this material, the nitrophenyl group and the carboxy group had a trans relationship across the double bond. The NMR spectrum (in $DMSO-d_6$) showed absorptions at 2.5 (d), 6.2 (m), and 7.9 (m) ppm.

Analysis: Calcd. for $C_{10}H_9NO_4$: C, 57.97; H, 4,38; N, 6.76%. Found: C, 57.92; H, 4.52; N, 6.87%.

The mother liquors from the above recrystallization were evaporated in vacuo, and the residue was recrystallized from acetonitrile. This afforded 13.8 g. of the title product, m.p. 147°-149° C. In this material, the nitrophenyl group and the carboxy group had a cis relationship across the double bond. The NMR spectrum (in perdeutero pyridine) showed absorptions at 2.0 (d), 6.1 (m), 7.25 (m) and 8.05 (m) ppm.

PREPARATION 13

2-Methyl-3-(3-Nitrophenyl)propenoic Acid

A mixture of 75 g. of 3-nitrobenzaldehyde, 98 g. of propionic anhydride and 48 g. of sodium propionate was heated at 170° to 175° C. for 1.25 hours, and then it was cooled and poured into 750 ml. of ice-water. Concentrated ammonium hydroxide was then added until a basic pH was obtained. The mixture was warmed on a steam bath for a few minutes and then the small amount of insoluble material was removed by filtration. The filtrate was acidified with concentrated hydrochloric acid and the solid was recovered by filtration. This crude product was recrystallized from aqueous ethanol to give 81 g. of the title compound, m.p. 200.5°–202° C.

PREPARATION 14

3-(3-Nitrophenyl)propenoly Chloride

A mixture of 50 g. of 3-(3-Nitrophenyl)propenoic acid, 24.54 ml. of thionyl chloride and 300 ml. of benzene were heated under reflux for 2.5 hours. The cooled solution was filtered and then it was evaporated in vacuo. The residue was recrystallized from carbon tetrachloride, to give 49.9 g. (91% yield) of the title compound, m.p. 81°–83.5° C.

PREPARATION 15

Starting with the appropriate propenoic or butenoic acid, and following substantially the procedure of Preparation 14, the following acid chlorides were prepared:
3-(4-nitrophenyl)propenoyl chloride (m.p. 150°–152° C.),
2-methyl-3-(4-nitrophenyl)propenoyl chloride (m.p. 87.5°–88.5° C.),
2-methyl-3-(3-nitrophenyl)propenoyl chloride and
3-(4-nitrophenyl)butenoyl chloride (m.p. 93°–96° C.).

PREPARATION 16

Starting with the appropriate propenoic or butenoic acid, and using the method of Preparation 14, the following acid chlorides can be prepared:
3-(2-nitrophenyl)-2-butenoyl chloride,
3-(3-nitrophenyl)-2-butenoyl chloride,
2methyl-3-(2-nitrophenyl)-2-butenoyl chloride,
2-methyl-3-(3-nitrophenyl)-2-butenoyl chloride,
2-methyl-3-(4-nitrophenyl)-2-butenoyl chloride and
2-methyl-3-(2-nitrophenyl)propenoyl chloride.

PREPARATION 17

N-(1-Methyldecyl)-3-(3-Nitrophenyl)propenamide

To a stirred solution of 31.0 g. of 2-aminoundecane in 100 ml. of tetrahydrofuran, was added a solution of 19.0 g. 3-(3-nitrophenyl)propenoyl chloride in 100 ml. of tetrahydrofuran, dropwise, during 75 minutes, at ca. 5° C. After the addition, the mixture was allowed to warm to room temperature, and stirring was continued for 45 minutes. The solvent was removed by evaporation in vacuo, and the residue was partitioned between ethyl acetate and water. The ethyl acetate layer was removed, washed successively with 1 N hydrochloric acid and water, and dried. Evaporation of the solvent in vacuo, followed by recrystallization of the residue from hexane, afforded 26 g. (83% yield) of the title product, m.p. 81°–83° C.

PREPARATION 18

Reaction of the appropriate acid chloride from Preparation 14 or Preparation 15 with the requisite alkylamine or cycloalkylamine, substantially according to Preparation 17, afforded the following compounds.

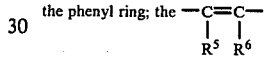

| $R^2$ | $R^5$ | $R^6$ | Position of nitro group* | Yield (%) | m.p. (°C.) |
|---|---|---|---|---|---|
| octyl | H | H | 4 | 53 | 95–97 |
| octyl | H | H | 3 | 45 | 76–78 |
| 1-methylheptyl | H | H | 4 | 92 | 68–70 |
| 1-methylheptyl | H | H | 3 | 66 | 69–71 |
| decyl | H | H | 4 | 79 | 106–108 |
| decyl | H | H | 3 | 30 | 97–99 |
| 1-methyldecyl | H | H | 4 | 84 | 91–94 |
| cycloheptyl | H | H | 4 | 73 | 180–182 |
| cycloheptyl | H | H | 3 | 88 | 144–145.5 |
| cyclododecyl | H | H | 4 | 96 | |
| cyclododecyl | H | H | 3 | | 185–187 |
| octyl | H | $CH_3$ | 4 | 90 | 71.5–72.5 |
| octyl | H | $CH_3$ | 3 | 100 | 58.5–59.5 |
| decyl | H | $CH_3$ | 4 | 94 | 79–80 |
| decyl | H | $CH_3$ | 3 | 92 | 65–66.5 |
| 1-methyldecyl | H | $CH_3$ | 4 | | 77.5–79.5 |
| cycloheptyl | H | $CH_3$ | 4 | 93 | 135–137 |
| decyl | $CH_3$ | H | 4 | 72 | |
| 1-methydecyl | $CH_3$ | H | 4 | 62 | |
| 1-methydecyl | $CH_3$ | H | 3 | 37 | |

*The numeral in this column indicates the position of the nitro group on the phenyl ring; the $-\underset{R^5}{C}=\underset{R^6}{C}-CO-NHR^2$ group is at the 1-position.

PREPARATION 19

By reacting the appropriate acid chloride from Preparations 14–16 with the requisite alkylamine or cycloalkylamine, the following compounds can be prepared:

| $R^2$ | $R^5$ | $R^6$ | Position of nitro group* |
|---|---|---|---|
| 6-methylheptyl | H | H | 2 |
| 1-pentylhexyl | H | H | 2 |
| dodecyl | H | H | 2 |
| pentadecyl | H | H | 3 |
| pentadecyl | H | H | 4 |
| 2-methyltetradecyl | H | H | 3 |
| cyclohexyl | H | H | 4 |
| cyclohexyl | H | H | 3 |
| nonyl | H | $CH_3$ | 2 |
| pentadecyl | H | $CH_3$ | 4 |
| cyclohexyl | H | $CH_3$ | 3 |
| cyclododecyl | H | $CH_3$ | 4 |
| octyl | $CH_3$ | H | 2 |
| tridecyl | $CH_3$ | H | 3 |
| pentadecyl | $CH_3$ | H | 4 |
| cyclohexyl | $CH_3$ | H | 4 |
| cyclodecyl | $CH_3$ | H | 2 |
| cyclododecyl | $CH_3$ | H | 3 |
| octyl | $CH_3$ | $CH_3$ | 2 |
| 1-methylnonyl | $CH_3$ | $CH_3$ | 3 |
| tridecyl | $CH_3$ | $CH_3$ | 4 |
| pentadecyl | $CH_3$ | $CH_3$ | 3 |
| cyclohexyl | $CH_3$ | $CH_3$ | 4 |
| cyclononyl | $CH_3$ | $CH_3$ | 2 |

-continued

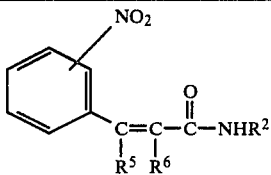

| $R^2$ | $R^5$ | $R^6$ | Position of nitro group* |
|---|---|---|---|
| cycloundecyl | CH$_3$ | CH$_3$ | 3 |
| cyclododecyl | CH$_3$ | CH$_3$ | 4 |

The numeral in this column indicates the position of the nitro group on the phenyl ring; the —C=C—CO—NHR$^2$ group is at the 1-position.
$\phantom{xxx}$ | $\phantom{x}$ |
$\phantom{xx}$R$^5$ R$^6$

PREPARATION 20

N-Octyl-3-(2-Nitrophenyl)propenamide

A mixture of 9.7 g. of 3-(2-nitrophenyl)propenoic acid, 5.6 g. of triethylamine and 240 ml. of dichloromethane was stirred at room temperature for 20 minutes, and then it was cooled in an ice-bath. To the mixture was then added, dropwise, during 15 minutes, a solution of 6.0 g. of ethyl chloroformate in 20 ml. of dichloromethane. After 15 minutes of stirring, a solution of 7.1 g. of octylamine in 20 ml. of dichloromethane was added dropwise, during 10 minutes. The reaction mixture was allowed to warm to room temperature, and then it was washed successively with 1 N potassium carbonate, 1 N hydrochloric acid, water and saturated sodium chloride. The resulting solution was dried and evaporated in vacuo, leaving 14.5 g. (95%) yield of the title compound as a tan solid.

PREPARATION 21

Starting with 3-(2-nitrophenyl)propenoic acid or 2-methyl-3-(3-nitrophenyl)propenoic acid, as appropriate, and decylamine or 1-methyldecylamine, as appropriate, and following substantially the procedure of Preparation 20, the following compounds were prepared as waxy solids, in essentially quantitative yield.

N-decyl-3-(2-nitrophenyl)propenamide,
N-(1-methyldecyl)-3-(2-nitrophenyl)propenamide,
N-decyl-2-methyl-3-(3-nitrophenyl)propenamide and
N-(1-methyldecyl)-2-methyl-3-(3-nitrophenyl)-propenamide.

PREPARATION 22

N-(1-Methyldecyl)-3-(3-Nitrophenyl)-2-butenamide

To a stirred slurry of 5.2 g. of the 3-(3-nitrophenyl)-2-butenoic acid from Preparation 12 having a melting point of 208°-210° C., in 100 ml. of dichloromethane, was added 2.8 g. of triethylamine in 10 ml. of dichloromethane. This was followed by the addition of a solution of 3.0 g. of ethyl chloroformate in 20 ml. of dichloromethane, during 20 minutes. Stirring was continued for 30 minutes, and then a solution of 1-methyldecylamine in 20 ml. of dichloromethane was added dropwise during 25 minutes. Stirring was continued overnight, and the the reaction mixture was washed successively with 1 N potassium carbonate, water and saturated sodium chloride. The resulting solution was dried using sodium sulfate, and then it was evaporated in vacuo leaving an oil which solidified on trituration under petroleum ether. This afforded 4.9 g. of the title compound, m.p. 72.5°–74° C.

PREPARATION 23

N-(1-Methyldecyl)-3-(3-Nitrophenyl)-2-butenamide

The 3-(3-nitrophenyl)-2-butenoic acid from Preparation 12 having a melting point of 147°-149° C. was reacted with ethyl chloroformate, followed by 1-methyldecylamine, according to the procedure of Preparation 22. This afforded a 72% yield of the title product.

PREPARATION 24

N-Decyl-3-(2-Aminophenyl)propenamide

A stirred solution of 15.3 g. of N-decyl-3-(2-nitrophenyl)propenamide in 200 ml. of glacial acetic acid was heated to 85° C. on a steam bath, and then 12.9 g. of iron powder was added portionwise, during 25 minutes. The reaction temperature was kept between 85° and 95° C. during the addition. The reaction mixture was filtered hot, and the residue was washed with hot glacial acetic acid. The cooled, combined acetic acid solutions were evaporated in vacuo, and the residue was dissolved in ethyl acetate. The ethyl acetate solution was washed several times with water and then with saturated sodium chloride solution. The resulting solution was dried using sodium sulfate, and then it was evaporated in vacuo to give the crude title product.

The crude product was chromatographed on ca. 350 g. of silica gel, eluting with 1% ethanol in chloroform. The appropriate fractions were combined and evaporated, and the residue was triturated with hexane, to give 10.5 g. of the title compound.

PREPARATION 25

Reduction of the appropriate nitro compound from Preparations 17, 18, 20 and 21 with iron powder in acetic acid, substantially according to Preparation 24, afforded the following compounds.

In many instances, the crude product was an oil, which was used in the next step without purification.

| $R^2$ | $R^5$ | $R^6$ | Position of amino group* | Chromatography** | Yield (%) | Melting Point (°C.) |
|---|---|---|---|---|---|---|
| octyl | H | H | 4 | No | 84 | oil |
| octyl | H | H | 3 | No | | oil |
| octyl | H | H | 2 | Yes | 85 | |
| 1-methylheptyl | H | H | 4 | No | 63 | oil |
| 1-methylheptyl | H | H | 3 | No | | oil |
| decyl | H | H | 4 | Yes | 50 | 107–109 |
| decyl | H | H | 3 | Yes | 69 | |
| 1-methyldecyl | H | H | 4 | Yes | 41 | 123–126 |
| 1-methyldecyl | H | H | 3 | Yes | 58 | |
| 1-methyldecyl | H | H | 2 | Yes | | 119–120.5 |
| cycloheptyl | H | H | 4 | No | 98 | gum |
| cyclo- | H | H | 3 | Yes | 67 | |

-continued

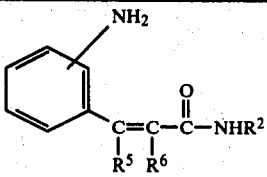

| R² | R⁵ | R⁶ | Position of amino group* | Chromatography** | Yield (%) | Melting Point (°C.) |
|---|---|---|---|---|---|---|
| heptyl | | | | | | |
| cyclododecyl | H | H | 4 | Yes | 54 | |
| cyclododecyl | H | H | 3 | Yes | | |
| octyl | H | CH₃ | 4 | No | 87 | gum |
| octyl | H | CH₃ | 3 | No | 82 | gum |
| decyl | H | CH₃ | 4 | Yes | 75 | 91.5–92.5 |
| decyl | H | CH₃ | 3 | Yes | 90 | 81.5–83.5 |
| 1-methyldecyl | H | CH₃ | 4 | No | 87 | 88–90 |
| 1-methyldecyl | H | CH₃ | 3 | Yes | 59 | |
| cycloheptyl | H | CH₃ | 4 | Yes | 95 | |
| decyl | CH₃ | H | 4 | Yes | 76 | oil |
| 1-methyldecyl | CH₃ | H | 4 | Yes | 81 | oil |
| 1-methyldecyl | CH₃ | H | 3 | No | 77 | oil |

*The numeral in this column indicates the position of the amino group on the phenyl ring; the —C(R⁵)=C(R⁶)—CO—NHR² group is at the 1-position.

**The entry "Yes" indicates that the product was purified by chromatography; the entry "No" indicates that the product was not purified by chromatography.

PREPARATION 26

By reduction of the appropriate nitro compound from Preparation 19, using iron and glacial acetic acid according to the procedure of Preparation 24, the following compounds can be prepared.

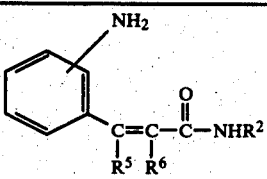

| R² | R⁵ | R⁶ | Position of amino group* |
|---|---|---|---|
| 6-methylheptyl | H | H | 2 |
| 1-pentylhexyl | H | H | 2 |
| dodecyl | H | H | 2 |
| pentadecyl | H | H | 3 |
| pentadecyl | H | H | 4 |
| 2-methyltetradecyl | H | H | 3 |
| cyclohexyl | H | H | 4 |
| cyclohexyl | H | H | 3 |
| nonyl | H | CH₃ | 2 |
| pentadecyl | H | CH₃ | 4 |
| cyclohexyl | H | CH₃ | 3 |
| cyclododecyl | H | CH₃ | 4 |
| octyl | CH₃ | H | 2 |
| tridecyl | CH₃ | H | 3 |
| pentadecyl | CH₃ | H | 4 |
| cyclohexyl | CH₃ | H | 4 |
| cyclodecyl | CH₃ | H | 2 |
| cyclododecyl | CH₃ | H | 3 |
| octyl | CH₃ | CH₃ | 2 |
| 1-methylnonyl | CH₃ | CH₃ | 3 |
| tridecyl | CH₃ | CH₃ | 4 |
| pentadecyl | CH₃ | CH₃ | 3 |

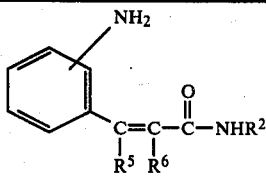

| R² | R⁵ | R⁶ | Position of amino group* |
|---|---|---|---|
| cyclohexyl | CH₃ | CH₃ | 4 |
| cyclononyl | CH₃ | CH₃ | 2 |
| cycloundecyl | CH₃ | CH₃ | 3 |
| cyclododecyl | CH₃ | CH₃ | 4 |

*The numeral in this column indicates the position of the amino group on the phenyl ring; the —C(R⁵)=C(R⁶)—CO—NHR² group is at the 1-position.

PREPARATION 27

N-(1-Methyldecyl)-3-(3-Aminophenyl)-2-butenamide

A stirred solution of 7.0 g. N-(1-methyldecyl)-3-(3-nitrophenyl)-2-butenamide (4.9 g. from Preparation 22 and 2.1 g. of substantially equivalent material from a similar preparation) in 80 ml. of glacial acetic acid was heated to 85° C. on a steam bath. To this solution was added portionwise, during 20 minutes, 5.4 g. of iron powder. The reaction mixture was filtered hot and the residue was washed with hot glacial acetic acid. The combined acetic acid solutions were evaporated in vacuo, and the residue was dissolved in ethyl acetate. The ethyl acetate solution was washed liberally with water, and then with saturated sodium chloride solution, and then it was dried using sodium sulfate. Removal of the solvent by evaporation in vacuo afforded the product as an oil.

The oil was purified by chromatography on ca. 280 g. of silica gel, eluting with a 1% solution of ethanol in ethyl acetate. The appropriate fractions were combined and evaporated, giving 5.8 g. of the title product, as an oil.

PREPARATION 28

N-(1-Methyldecyl)-3-(3-Aminophenyl)-2-butenamide

The N-(1-methyldecyl)-3-(3-nitrophenyl)-2-butenamide from Preparation 23 (6.5 g.) was reduced with iron powder (5.0 g.) in glacial acetic acid (80 ml.) in a manner analogously to Preparation 27. After chromatography, 4.5 g. of the title compound was obtained, as an amber oil.

I claim:

1. An alkenamide compound of the formula

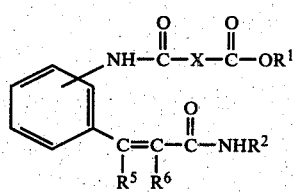

and the pharmaceutically-acceptable salts thereof; wherein R¹ is selected from the group consisting of hydrogen, alkyl having 1 to 4 carbons, and -CH₂-CH₂-NR³R⁴, wherein R³ and R⁴ are each alkyl having 1 to 3 carbons;

$R^2$ is selected from the group consisting of alkyl having 8 to 15 carbons and cycloalkyl having from 6 to 12 carbons;

$R^5$ and $R^6$ are selected from the group consisting of hydrogen and methyl;

and X is selected from the group consisting of cis-vinylene, ethylene and

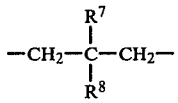

wherein $R^7$ and $R^8$ are each selected from the group consisting of hydrogen and methyl.

2. A compound according to claim 1, wherein X is cis-vinylene.

3. A compound according to claim 2, wherein $R^1$ is hydrogen.

4. A compound according to claim 3, wherein $R^2$ is said alkyl.

5. A compound according to claim 4, wherein $R^5$ and $R^6$ are both hydrogen.

6. A compound according to claim 5, wherein the two substituents on the phenyl ring have a meta relationship to each other.

7. The compound according to claim 6, wherein $R^2$ is decyl.

8. The compound according to claim 6, wherein $R^2$ is undecyl.

9. A compound according to claim 4, wherein $R^5$ is hydrogen and $R^6$ is methyl.

10. A compound according to claim 9, wherein the two substituents on the phenyl ring have a meta relationship to each other.

11. The compound according to claim 10, wherein $R^2$ is decyl.

12. The compound according to claim 10, wherein $R^2$ is 1-methyldecyl.

13. A compound according to claim 4, wherein $R^5$ is methyl and $R^6$ is hydrogen.

14. The compound according to claim 13, wherein $R^2$ is 1-methyldecyl and the substituents on the phenyl ring have a meta relationship to each other.

15. A compound according to claim 1, wherein X is ethylene.

16. A compound according to claim 15, wherein $R^1$ is hydrogen.

17. A compound according to claim 16, wherein $R^2$ is said alkyl.

18. The compound according to claim 17, wherein $R^2$ is decyl, $R^5$ is hydrogen, $R^6$ is methyl and the two substituents on the phenyl ring have a meta relationship to each other.

19. A compound according to claim 1, wherein X is

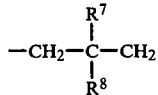

20. A compound according to claim 19, wherein $R^1$ is hydrogen.

21. A compound according to claim 20, wherein $R^2$ is said alkyl.

22. A compound according to claim 21, wherein $R^7$ and $R^8$ are each hydrogen.

23. The compound according to claim 22, wherein $R^2$ is decyl, $R^5$ is methyl, $R^6$ is hydrogen and the two substituents on the phenyl ring have a meta relationship to each other.

24. A compound according to claim 21, wherein $R^7$ and $R^8$ are both methyl.

25. The compound according to claim 24, wherein $R^2$ is decyl, $R^5$ and $R^6$ are both hydrogen, and the two substituents on the phenyl ring have a para relationship to each other.

26. The method of antagonizing the effect of slow-reacting substance of anaphylaxis in a human subject, which comprises administering thereto a slow-reacting substance of anaphylaxis antagonizing amount of an alkenamide compound of the formula

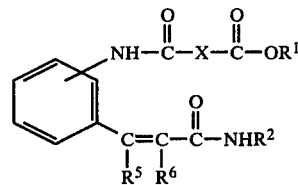

or a pharmaceutically-acceptable salt thereof;
wherein $R^1$ is selected from the group consisting of hydrogen, alkyl having 1 to 4 carbons, and —CH$_2$—CH$_2$—NR$^3$R$^4$, wherein $R^3$ and $R^4$ are each alkyl having 1 to 3 carbons;

$R^2$ is selected from the group consisting of alkyl having 8 to 15 carbons and cycloalkyl having from 6 to 12 carbons;

$R^5$ and $R^6$ are selected from the group consisting of hydrogen and methyl;

and X is selected from the group consisting of cis-vinylene, ethylene and

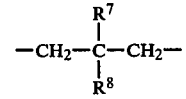

wherein $R^7$ and $R^8$ are each selected from the group consisting of hydrogen and methyl.

27. A pharmaceutical composition, which comprises a pharmaceutically-acceptable carrier and an alkenamide compound of the formula

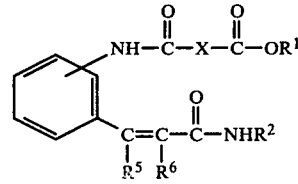

or a pharmaceutically-acceptable salt thereof;
wherein $R^1$ is selected from the group consisting of hydrogen, alkyl having 1 to 4 carbons, and —CH$_2$—CH$_2$—NR$^3$R$^4$, wherein $R^3$ and $R^4$ are each alkyl having 1 to 3 carbons;

$R^2$ is selected from the group consisting of alkyl having 8 to 15 carbons and cycloalkyl having from 6 to 12 carbons;

$R^5$ and $R^6$ are selected from the group consisting of hydrogen and methyl;

and X is selected from the group consisting of cis-vinylene, ethylene and
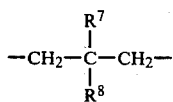
wherein $R^7$ and $R^8$ are each selected from the group consisting of hydrogen and methyl;
and wherein the ratio of the pharmaceutically-acceptable carrier to the alkenamide compound is in the range from 1:6 to 6:1 by weight.